US010744759B2

(12) United States Patent
Baldy, Jr. et al.

(10) Patent No.: US 10,744,759 B2
(45) Date of Patent: Aug. 18, 2020

(54) FIRST DROP DISSIMILARITY IN DROP-ON-DEMAND INKJET DEVICES AND METHODS FOR ITS CORRECTION

(75) Inventors: William J. Baldy, Jr., Telford, PA (US); Amin Famili, Orefield, PA (US); Saurabh A. Palkar, Audubon, PA (US)

(73) Assignee: Cardinal Health Switzerland 515 GmbH, Bar Zug (CH)

( * ) Notice: Subject to any disclaimer, the term of this patent is extended or adjusted under 35 U.S.C. 154(b) by 610 days.

(21) Appl. No.: 12/825,428

(22) Filed: Jun. 29, 2010

(65) Prior Publication Data

US 2011/0316919 A1    Dec. 29, 2011

(51) Int. Cl.
*B05D 1/18* (2006.01)
*B41J 2/045* (2006.01)
*A61F 2/91* (2013.01)

(52) U.S. Cl.
CPC ......... *B41J 2/0456* (2013.01); *B41J 2/04586* (2013.01); *A61F 2/91* (2013.01)

(58) Field of Classification Search
CPC ........ B01D 1/18; B05B 17/0615; C04B 40/04
USPC ..... 427/2.1–2.3; 347/15, 19, 73–83; 702/85, 702/101, 102
See application file for complete search history.

(56) References Cited

U.S. PATENT DOCUMENTS

| 4,897,665 A | 1/1990 | Aoki |
|---|---|---|
| 5,285,215 A | 2/1994 | Liker |
| 5,642,142 A | 6/1997 | Bohorquez |
| 6,029,896 A | 2/2000 | Self et al. |
| 6,241,762 B1 | 6/2001 | Shanley |
| 6,502,915 B1 | 1/2003 | Feinn et al. |
| 6,548,308 B2 | 4/2003 | Ellson et al. |
| 6,833,156 B2 | 12/2004 | Miyashita et al. |
| 7,208,010 B2 | 4/2007 | Shanley et al. |
| 7,458,669 B2 | 12/2008 | Jones et al. |
| 7,658,758 B2 | 2/2010 | Diaz et al. |
| 2001/0001050 A1 | 5/2001 | Miyashita et al. |
| 2002/0037375 A1 | 3/2002 | Ellson et al. |
| 2002/0089561 A1 | 7/2002 | Weitzel et al. |
| 2003/0081040 A1 | 5/2003 | Therien |
| 2004/0133960 A1 | 6/2004 | Usui |
| 2004/0238978 A1 | 12/2004 | Diaz |
| 2005/0003283 A1 | 1/2005 | Kawase et al. |
| 2006/0073265 A1 | 4/2006 | Teichman et al. |

(Continued)

FOREIGN PATENT DOCUMENTS

| CN | 1310930 | 8/2001 |
|---|---|---|
| CN | 1366205 | 8/2002 |

(Continued)

OTHER PUBLICATIONS

Verkouteren et al., Inkjet Metrology: High-Accuracy Mass Measurements of Microdroplets Produced by a Drop-on-Demand Dispenser, Anal. Chem. 2009, 81, 8577-8584.*

(Continued)

*Primary Examiner* — Hai Y Zhang
(74) *Attorney, Agent, or Firm* — Dergosits & Noah LLP; Todd A. Noah

(57) ABSTRACT

A number of methods may be utilized to correct for the first drop dissimilarity in drop-on-demand inkjet devices. Various collection processes, mass calculations and timing manipulation may be utilized to correct the first drop dissimilarity problem.

1 Claim, 9 Drawing Sheets

(56) References Cited

U.S. PATENT DOCUMENTS

| | | | |
|---|---|---|---|
| 2006/0217801 A1 | 9/2006 | Rosenthal | |
| 2006/0279613 A1 | 12/2006 | Jones et al. | |
| 2007/0082120 A1* | 4/2007 | Diaz et al. | A61L 33/00 427/2.24 |
| 2008/0088663 A1 | 4/2008 | Kojima | |
| 2010/0073413 A1* | 3/2010 | Mataki | B41J 2/2132 347/9 |
| 2012/0263867 A1 | 10/2012 | Kanbe et al. | |

FOREIGN PATENT DOCUMENTS

| | | |
|---|---|---|
| CN | 1688265 | 10/2005 |
| CN | 1688265 A | 10/2005 |
| CN | 1876382 | 12/2006 |
| CN | 1905157 | 1/2007 |
| CN | 101048236 | 10/2007 |
| JP | 2004-154763 | 6/2004 |
| JP | 2005231190 | 9/2005 |
| JP | 2009-513181 | 4/2009 |
| WO | 9808687 | 3/1998 |
| WO | 98008687 A1 | 3/1998 |
| WO | WO9808687 * | 3/1998 |
| WO | 2004/026182 | 4/2004 |
| WO | 2004-049466 | 10/2004 |

OTHER PUBLICATIONS

U.S. Appl. No. 12/855,296, filed Aug. 27, 2010, William J. Baldy et al.

U.S. Appl. No. 12/891,193, filed Sep. 27, 2010, William J. Baldy et al.

Drews, R.E. IS&T's Int. Congr. Adv. Non-Impact Print. Technol., 7$^{th}$, Portland, OR, 1991.

Fagerquist, R. IS&T's Int. Congr. Adv. Non-Impact Print. Technol., 7$^{th}$, Portland, OR, 1991.

Fan, K.-C. et al., J. Opt. A: Pure Appl. Opt. 2009, 11, 015503.

Jackson, A.C. et al., Appl. Physiol. 1997, 43, 523-536.

Hugli, H. et al., Machine Vision Applications in Industrial Inspection VIII—Proc. SPIE. 2000, 11, 60-67.

Bogden, V.A. et al., "Acoustic Phenomena in a Demand Mode Piezoelectric Ink jet Printer", *J. Imaging Sci. Technol.* 2002, 46, No. 5, 409-414.

Bogy, D.B. et al., "Experimental and Theoretical Study of Wave Propagation Phenomena in Drop-on-Demand Ink Jet Devices", *IBM J. Res. Develop.* 1984, 28, No. 3, 314-321.

Boland, T. et al., "Application of inkjet printing to tissue engineering", *Biotechnol. J.* 2006, 1, 910-917.

Calvert, P., "Inkjet Printing for Materials and Devices", *Chem. Mater.* 2001, 13, 3299-3305.

Dong, H, et al., "An experimental study of drop-on-demand drop formation", *Phys. Fluids,* 2006, 18, 072102.

Dong, H. et al., "Visualization of drop-on-demand inkjet: Drop formation and deposition," *Rev. Sci. Instrum.* 2006, 77, 085101-085108.

Dong, H., Ph.D. Thesis, Georgia Institute of Technology, 2006.

Feng, J.Q., "A General Fluid Dynamic Analysis of Drop Ejection in Drop-on-Demand Ink Jet Devices," *J. Imaging Sci. Technol.* 2002, 46, No. 5, 398-408.

Jo, B.W. et al., "Evaluation of jet performance in drop-on-demand (DOD) inkjet printing", *Korean J. Chem. Eng.* 2009, 26(2), 339-348.

Kang, H.R., "Water-Based Ink-Jet Ink. III," *J. Imaging Sci.* 1991, 35, No. 3, 195-201.

Lee, E.R., *Microdrop Generation*; CRC Press LLC: Boca Raton, 2003.

Lemmo, A.V. et al., "Inkjet dispensing technology: applications in drug discovery",*Curr. Opin. Biotechnol.* 1998, 9, 615-617.

Martin, G.D. et al., "Inkjet printing—the physics of manipulating liquid jets and drops", *J. Phys. Conf. Series.* 2008, 105, 012001.

MicroFab Technologies, Inc., Plano, TX. Technical Notes No. 99-01. "Background on Ink-Jet Technology" (1999) http://www.microfab.com/equipment/technotes/technote99-01.pdf.

MicroFab Technologies, Inc., Plano, TX. Technical Notes No. 99-03. "Drive Waveform Effects on Ink-Jet Device Performance" (1999) http://www.microfab.com/equipment/technotes/technote99-03.pdf.

MicroFab Technologies, Inc., Plano, TX. Technical Notes. "Satellites occurrence and approaches to eliminate them" (2007) http://www.microfab.com/equipment/technotes/Satellites_version_09_26_07.pdf.

Shore, H.J. et al., "The effect of added polymers on the formation of drops ejected from a nozzle" Phys. Fluids. 2005, 17, 033104.

Singh, M, et al., Inkjet Printing-Process and Its Applications, Adv. Mater. 2010, 22, 673-685.

Verkouteren, R.M, et al., "Inkjet Metrology: High-Accuracy Mass Measurements of Microdroplets Produced by a Drop-on-Demand Dispenser", *Anal. Chem.* 2009, 81, 8577-8584.

Weiss, L. E, et al., "Inkjet Deposition System With Computer Vision-Based Calibration for Targeting Accuracy" [Online] Carnegie Mellon University Technical Report CMU-RI-TR-06-15, 2006.

Wijshoff, H., "Free surface flow and acousto-elastic interaction in piezo inkjet", Technical notes from Océ Technologies B.V., Venlo, The Netherlands, 215-218, 2004.

Wu, H-C, "Development of a three-dimensional simulation system for micro-inkjet and its experimental verification", *Mat. Sci. and Eng. A.* 2004, 373, 268-278.

Office Action dated Jul. 2, 2014 in corresponding Chinese Patent Application No. 201110191562.5.

Search Report dated Jun. 24, 2014 in Chinese Patent Application No. 201110191562.5.

Notification for Reasons for Refusal in corresponding Japanese Patent Application No. 2011-142724 dated Mar. 24, 2015.

Office Action in corresponding Chinese Patent Application No. 201110191562.5 dated Jul. 2, 2014.

Search Report in corresponding Chinese Patent Application No. 201110191562.5 dated Jul. 2, 2014.

Office Action for co-pending Japan Application No. 2011-142724; dated Dec. 1, 2015.

First Examination Report for India Patent Application No. 666/KOL/2011, dated Jan. 12, 2018.

* cited by examiner

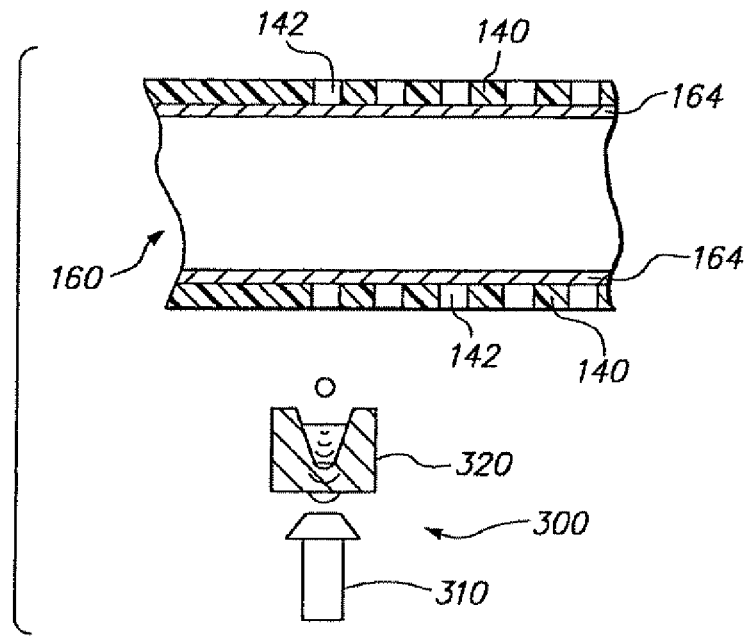
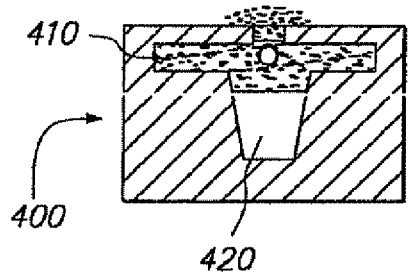
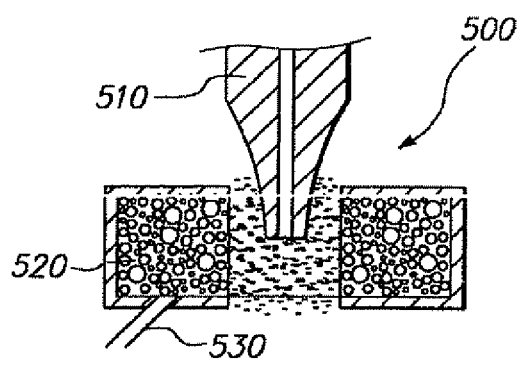

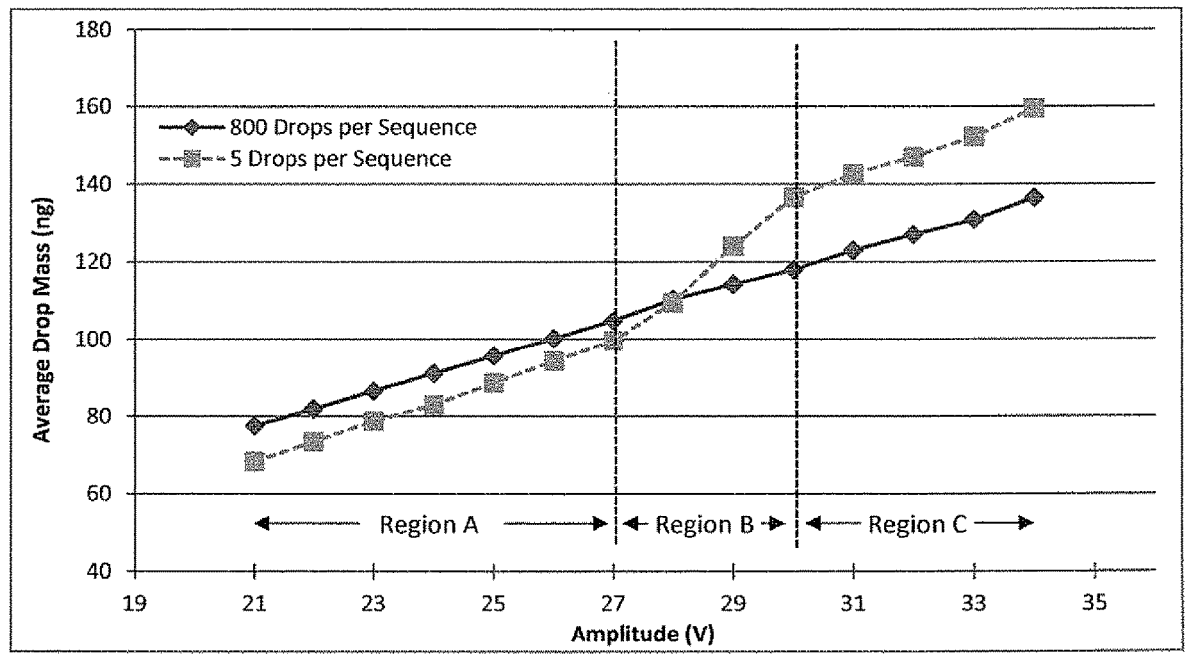
FIG. 14
FIG. 15
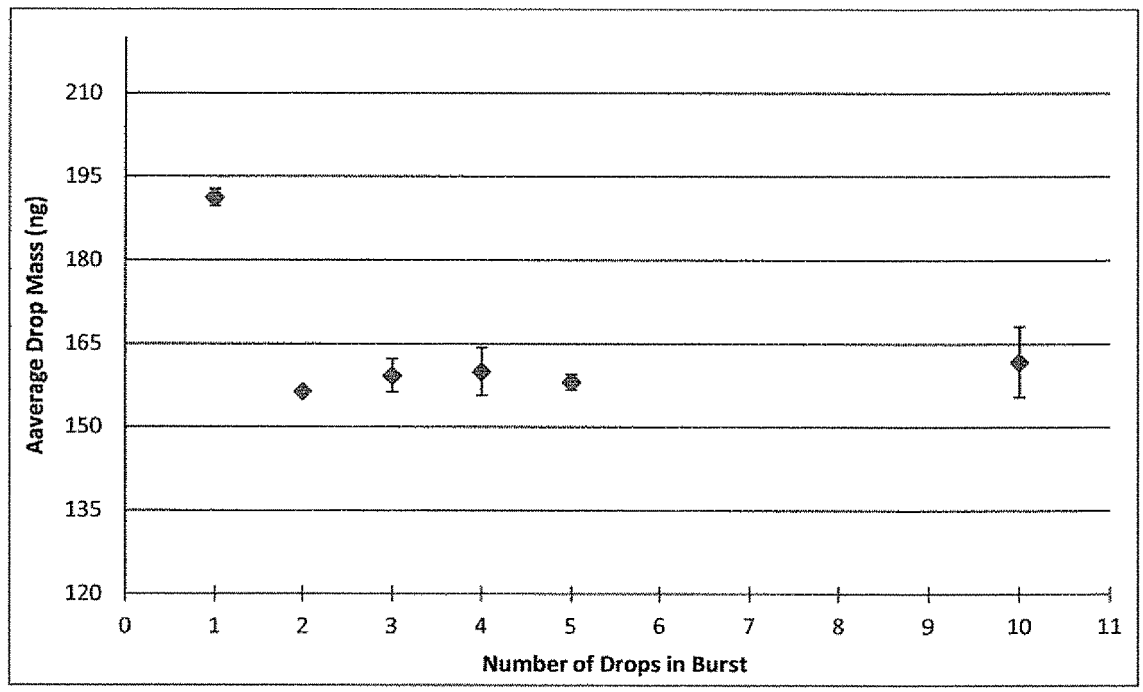

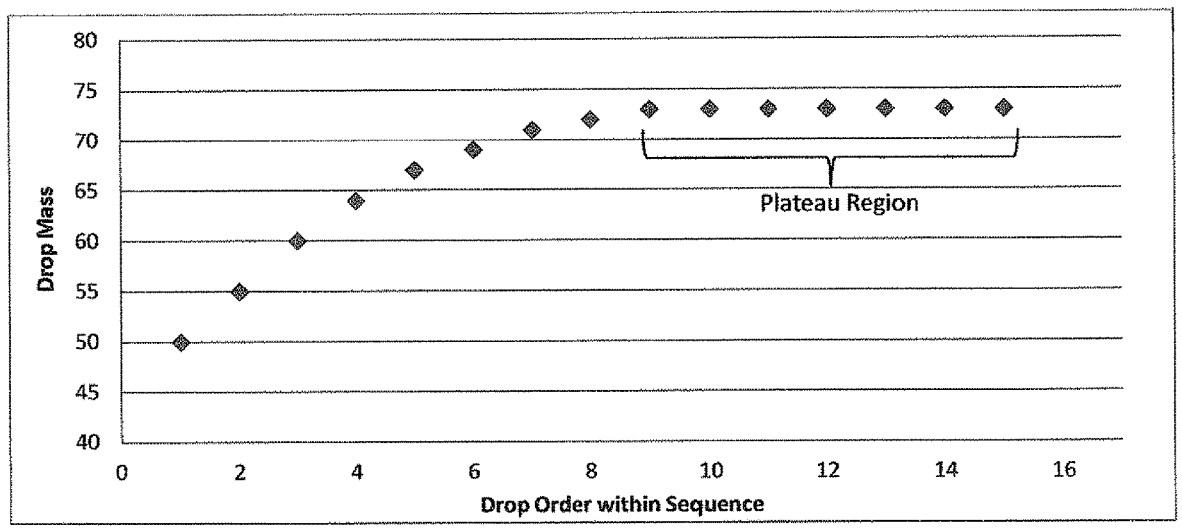
*FIG. 17*
*FIG. 18*
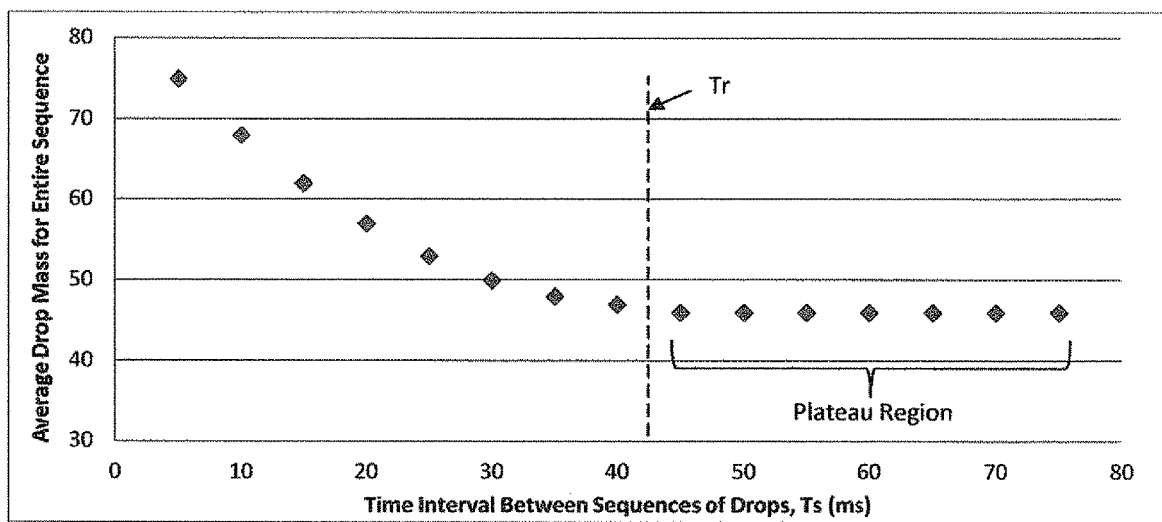

FIRST DROP DISSIMILARITY IN DROP-ON-DEMAND INKJET DEVICES AND METHODS FOR ITS CORRECTION

BACKGROUND OF THE INVENTION

1. Field of the Invention

The present invention relates to methods for loading beneficial agents into implantable medical devices, and more particularly to methods for improving inkjet printing technology, specifically inkjet printing precision, with respect to loading beneficial agents into implantable medical devices.

2. Discussion of the Related Art

A common operational mode in inkjet technology, known as drop-on-demand ejection, is used as a way to deliver a controlled quantity of material to a precise location on a target. This operational mode employs the ejection of individual or the ejection of a sequence (burst) of drops based on a timed trigger event. For applications such as electronics, drug-device combinations and the like, the precision in location and amount of material delivered is critical to have a quality product since only about 1 to 10 drops are delivered at every location. Hence to accurately target the amount of material delivered, one needs to know the exact mass of every drop that is being deposited.

Since individual drops weigh in the range of 10 ng to 1 ug, it is very difficult to determine their mass accurately, even in an off-line mode. This problem is further complicated by complex geometry and machine design used for the actual deposition of drops. Hence on-line measurement of drop size and feedback control during deposition is extremely challenging. As a result, a calibration scheme is employed where a large number of drops (5000 to 20000) is collected and weighed to determine the average mass of ejected drops. This scheme assumes that the drop mass remains the same no matter how many drops are ejected. Some recent publications have shown that this assumption is not valid and the first few drops ejected in a stream of drops have lower mass. Because of this discrepancy between calibration and actual deposition, the actual product may not receive the correct amount of the desired substance.

It has also been found in the course of experimentation related to the present invention that the weight of the first few drops changes as a function of the voltage amplitude used to create these drops. Hence the difference between the average mass calculated using the above calibration procedure and the average mass of the first 1 to 20 (approximately) drops changes as a function of voltage amplitude.

Accordingly, there exists a need for overcoming the disadvantages associated with the current technology by developing a methodology for depositing the exact same amount of a particular substance at various well defined locations on an object of interest.

SUMMARY OF THE INVENTION

The method for correction of first drop dissimilarity in drop-on-demand inkjet devices in accordance with the present invention overcomes the limitations as briefly described above.

In accordance with a first aspect, the present invention is directed to a method for depositing the same, accurately determined amount of a particular substance at one or more locations on an object. The method comprising the steps of positioning an object in proximity to at least one jet of an ink-jet dispensing unit such that relative movement between the object and the at least one jet is achievable, collecting a first predetermined number of drops of a particular substance from the at least one jet in a receptacle and determine the average drop mass, calculating how many drops are required to achieve a desired drop mass at each of the one or more locations on the object, collecting a second predetermined number of drops of the particular substance from the at least one jet in a receptacle, until steady state drop size is achieved, and depositing a number of drops required to achieve the desired drop mass at each of the one or more locations on the object while ensuring that the time needed to move between target locations is less than or equal to the time interval between consecutive drops.

In accordance with another object, the present invention is directed to a method for depositing the same, accurately determined, amount of a particular substance at one or more locations on an object. The method comprising the steps of positioning an object in proximity to at least one jet of an ink-jet dispensing unit such that relative movement between the object and the at least one jet is achievable, collecting a first predetermined number of drops of the particular substance from the at least one jet in a receptacle and determine the average drop mass, while ensuring that the time between bursts of drops is greater than the time to achieve consistent first drop mass, calculating how many drops are required to achieve a desired drop mass at each of the one or more locations on the object, and depositing a burst of drops equal to the desired drop mass at each of the one or more locations on the object while ensuring that the time between bursts of drops is greater than the time to achieve consistent first drop mass.

In accordance with yet another object, the present invention is directed to a method for depositing the same, accurately determined, amount of a particular substance at one or more locations on an object. The method comprising positioning an object in proximity to at least one jet of an ink-jet dispensing unit such that relative movement between the object and the at least one jet is achievable, determining the relationship between average drop mass and device driving waveform amplitude for a first operational mode comprising a first process-relevant number of drops per burst, determining the relationship between average drop mass and device driving waveform amplitude for a second operational mode comprising a second number of drops per burst to facilitate rapid and accurate ink-jet drop-mass calibration, wherein the second number is larger than the first number, calculating a difference between the first and second operational modes, and compensating for the difference between the first and second operational modes by applying the difference to an actual deposition process and depositing a burst of drops at each of the one or more locations on the object.

Drop-on-demand operation of inkjet devices provides a simple way to precisely control the quantity of material reaching a target. However, it has been shown here that significantly more characterization is required to implement drop-on-demand dispensing than is required for continuous dispensing operations. This is largely a result of the dissimilarity between the first drop ejected and subsequent drops, where the first drop is often different in morphology and trajectory, both of which would affect the ability to accurately reach the target, as well as in mass, which would impact dispensing accuracy. This will be of greatest concern to applications in which small quantities of drops are deposited on various points along a target, as it is small drop bursts that are the most sensitive to effects introduced by the first drop. Because the size of the first drop relative to those that follow is a function of driving amplitude, neither the direction nor the magnitude of the bias introduced by this effect will be consistent and, thus, cannot be accounted for mathematically. A carefully-designed dispensing protocol backed by thorough inkjet characterization for the particular solution of interest is the recommended method to account for these effects.

The present invention is directed to methods for depositing the exact same amount of a particular substance at various well defined locations on an object of interest. The methods are easy to implement, efficient and cost effective.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 7 is a side cross-sectional view of an acoustic dispenser for delivery of a beneficial agent to an expandable medical device.

FIG. 8 is a side cross-sectional view of an alternative acoustic dispenser reservoir.

FIG. 9 is a side cross-sectional view of an alternative piezoelectric dispenser system.

FIG. 14 is a plot of the average drop weight as a function of driving amplitude for the different numbers of drops in a sequence in accordance with the present invention.

FIG. 15 is a plot of the average drop mass as a function of quantity of drops in a burst in Region A as defined in FIG. 14 in accordance with the present invention.

FIG. 17 is a plot of the drop mass as a function of order of ejection within a burst in accordance with the present invention.

FIG. 18 is a plot of the average drop mass for an entire sequence of drops as a function of time between adjacent bursts in accordance with the present invention.

DETAILED DESCRIPTION OF THE PREFERRED EMBODIMENTS

Figure 1:
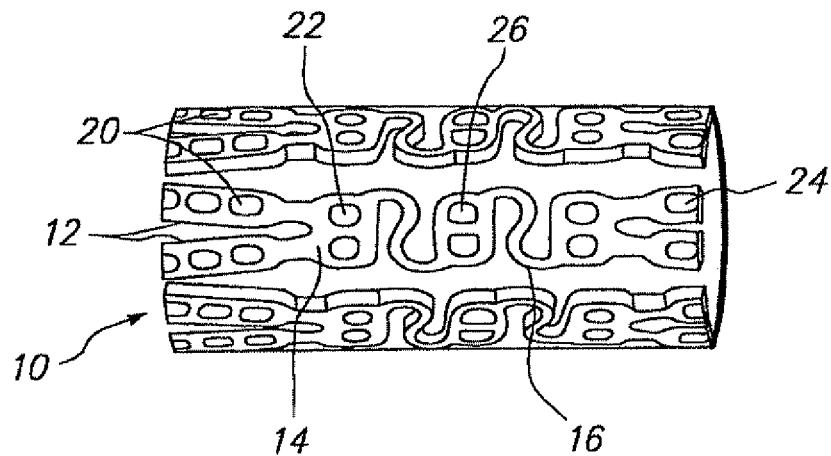
FIG. 1 is a perspective view of a therapeutic agent delivery device in the form of an expandable stent.

The present invention relates to a method and apparatus for loading a beneficial agent into an expandable medical device. More particularly, the invention relates to a method and apparatus for loading a beneficial agent in a stent.

The term "beneficial agent" as used herein is intended to have its broadest possible interpretation and is used to include any therapeutic agent or drug, as well as inactive agents such as barrier layers, carrier layers, therapeutic layers, protective layers or combinations thereof.

The terms "drug" and "therapeutic agent" are used interchangeably to refer to any therapeutically active substance that is delivered to a bodily conduit of a living being to produce a desired, usually beneficial, effect. The present invention is particularly well suited for the delivery of antineoplastic, angiogenic factors, immuno-suppressants, anti-inflammatories and antiproliferatives (anti-restenosis agents) such as paclitaxel and Rapamycin for example, and antithrombins such as heparin, for example.

The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent, a therapeutic agent, an activating agent or a deactivating agent, as defined herein. A matrix is also a medium that may simply provide support, structural integrity or structural barriers. The matrix may be polymeric, non-polymeric, hydrophobic, hydrophilic, lipophilic, amphiphilic, and the like.

The term "bioresorbable" refers to a matrix, as defined herein, that can be broken down by either chemical or physical process, upon interaction with a physiological environment. The bioresorbable matrix is broken into components that are metabolizable or excretable, over a period of time from minutes to years, preferably less than one year, while maintaining any requisite structural integrity in that same time period.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semi-synthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000.

The term "openings" refers to holes of any shape and includes both through-openings, blind holes, slots, channels and recesses.

The term "shot" or "drop" herein refers to the material ejected from an inkjet dispenser, inkjet, or micro-jetting dispenser as a result of a single voltage pulse to the piezoelectric element within the inkjet. After the material is ejected from the inkjet, it may fragment into smaller masses herein referred to as "droplets". In addition, the terms inkjet dispenser, inkjet, inkjet dispensing unit, micro-jetting dispenser and the like may be used interchangeably.

FIG. 1 illustrates a medical device 10 according to the present invention in the form of a stent design with large, non-deforming struts 12 and links 14, which may contain openings (or holes) 20 without compromising the mechanical properties of the struts or links, or the device as a whole. The non-deforming struts 12 and links 14 may be achieved by the use of ductile hinges which are described in detail in U.S. Pat. No. 6,241,762 which is incorporated hereby by reference in its entirety. The holes 20 serve as large, protected reservoirs for delivering various beneficial agents to the tissue in the area of the tissue in the area of the device implantation site.

As shown in FIG. 1, the openings 20 may be circular 22, rectangular 24, or D-shaped 26 in nature and form cylindrical, rectangular, or D-shaped holes extending through the width of the medical device 10. It may be appreciated that the openings 20 may be other shapes without departing from the present invention. In addition, the holes or reservoirs do not have to be through holes as described above.

The volume of beneficial agent that may be delivered using openings 20 is about 3 to 10 times greater than the volume of a 5 micron coating covering a stent with the same stent/vessel wall coverage ratio. This much larger beneficial agent capacity provides several advantages. The larger capacity may be used to deliver multi-drug combinations, each with independent release profiles, for improved efficacy. Also, larger capacity can be used to provide larger quantities of less aggressive drugs and to achieve clinical efficacy without the undesirable side-effects of more potent drugs, such as retarded healing of the endothelial layer.

Figure 2:
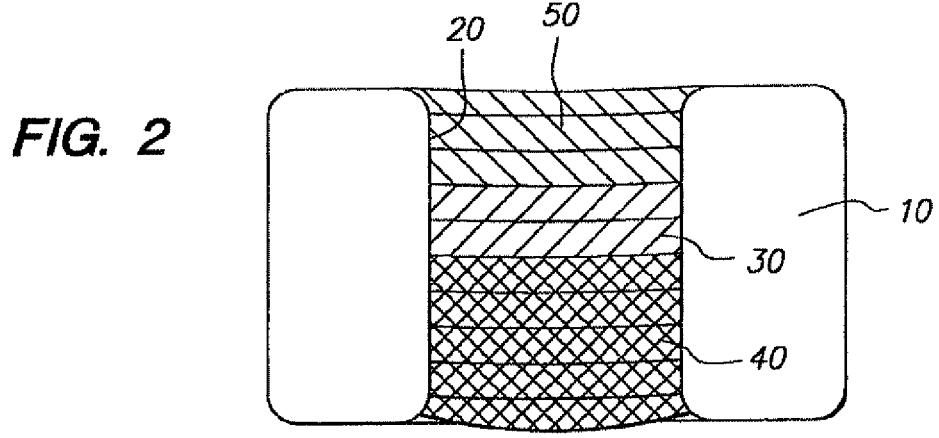
FIG. 2 is a cross-sectional view of a portion of a therapeutic agent delivery device having a beneficial agent contained in an opening in layers.

FIG. 2 shows a cross-section of a medical device 10 in which one or more beneficial agents have been loaded into the opening 20 in layers. Examples of some methods of creating such layers and arrangements of layers are described in U.S. Pat. No. 7,208,010, issued on Apr. 24, 2007, which is incorporated herein by reference in its entirety. Although the layers are illustrated as discrete layers, the layers can also mix together upon delivery to result in an inlay of beneficial agent with concentration gradients of therapeutic agents but without distinct boundaries between layers.

According to one example, the total depth of the opening 20 is about 100 to about 140 microns, typically 125 microns and the typical layer thickness would be about 2 to about 50 microns, preferably about 12 microns. Each typical layer is thus individually about twice as thick as the typical coating applied to surface-coated stents. There would be at least two and preferably about ten to twelve such layers in a typical opening, although this amount may be tailored to the particular need, with a total beneficial agent thickness about 25 to 28 times greater than a typical surface coating. According to one preferred embodiment of the present invention, each of the openings have an area of at least $5 \times 10^{-6}$ square inches, and preferably at least $7 \times 10^{-6}$ square inches. Typically, the openings are filled about 50 percent to about 75 percent full of beneficial agent.

Since each layer is created independently, individual chemical compositions and pharmacokinetic properties can be imparted to each layer. Numerous useful arrangements of such layers can be formed, some of which will be described below. Each of the layers may include one or more agents in the same or different proportions from layer to layer. The layers may be solid, porous, or filled with other drugs or excipients. As mentioned above, although the layers are deposited separately, they may mix forming an inlay without boundaries between layers, potentially resulting in a transition gradient within the inlay.

As shown in FIG. 2, the opening 20 is filled with a beneficial agent. The beneficial agent includes a barrier layer 40, a therapeutic layer 30, and a cap layer 50.

Alternatively, different layers could be comprised of different therapeutic agents altogether, creating the ability to release different therapeutic agents at different points in time. The layers of beneficial agent provide the ability to tailor a delivery profile to different applications. This allows the medical device according to the present invention to be used for delivery of different beneficial agents to a wide variety of locations in the body.

A protective layer in the form of a cap layer 50 is provided at a tissue contacting surface of a medical device. The cap layer 50 can block or retard biodegradation of subsequent layers and/or blocks or retards diffusion of the beneficial agent in that direction for a period of time which allows the delivery of the medical device to a desired location in the body. When the medical device 10 is a stent which is implanted in a lumen, the barrier layer 40 is positioned on a side of the opening 20 facing the inside of the lumen. The barrier layer 40 prevents the therapeutic agent 30 from passing into the lumen and being carried away without being delivered to the lumen tissue. Alternately, there may be instances where preferential directional drug delivery into the lumen is warranted, in those cases the barrier layer 40 may be positioned on a side of the openings 20 facing the tissue, thus preventing the therapeutic agent 30 from facing into the tissue.

Typical formulations for therapeutic agents incorporated in these medical devices are well known to those skilled in the art.

Although the present invention has been described with reference to a medical device in the form of a stent, the medical devices of the present invention can also be medical devices of other shapes useful for site-specific and time-release delivery of drugs to the body and other organs and tissues. The drugs may be delivered to the vasculature including the coronary and peripheral vessels for a variety of therapies, and to other lumens in the body. The drugs may increase lumen diameter, create occlusions, or deliver the drug for other reasons.

Medical devices and stents, as described herein, are useful for the prevention of amelioration of restenosis, particularly after percutaneous transluminal coronary angioplasty and intraluminal stent placement. In addition to the timed or sustained release of anti-restenosis agents, other agents such as anti-inflammatory agents may be incorporated into the multi-layers incorporated in the plurality of holes within the device. This allows for site-specific treatment or prevention any complications routinely associated with stent placements that are known to occur at very specific times after the placement occurs.

Figure 3:
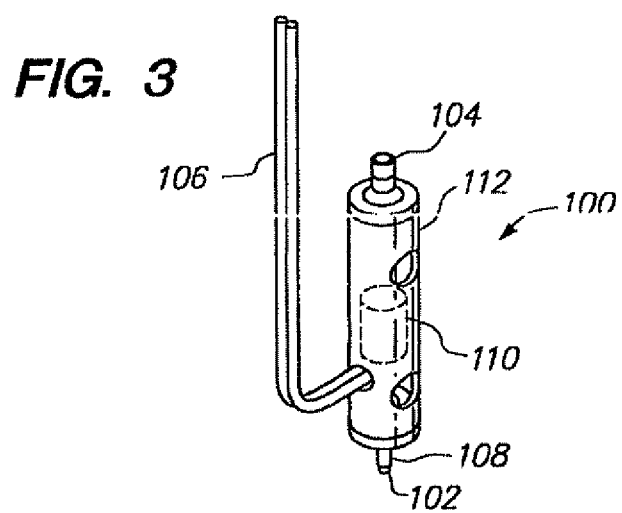
FIG. 3 is a side view of a piezoelectric micro-jetting dispenser for delivery of a beneficial agent.

FIG. 3 shows a piezoelectric micro-jetting dispenser 100 used to dispense a beneficial agent into the opening of a medical device. The dispenser 100 has a capillary tube 108 having a fluid outlet or orifice 102, a fluid inlet 104, and an electrical cable 106. The piezoelectric dispenser 100 preferably includes a piezo crystal 110 within a housing 112 for dispensing a fluid drop through the orifice 102. The crystal 110 surrounds a portion of the capillary tube 108 and receives an electric charge that causes the crystal to vibrate. When the crystal vibrates inward, it forces a tiny amount of fluid out of the fluid outlet 102 of the tube 108 to fill an opening 20 in a medical device. In addition, when the crystal vibrates outward, the crystal pulls additional fluid into the tube 108 from a fluid reservoir connected to the inlet 104 to replace the fluid that has been dispensed into the opening of the medical device.

In the exemplary embodiment as shown in FIG. 3, the micro-jetting dispenser 100 includes an annular piezoelectric (PZT) actuator 110 bonded to a glass capillary tube 108. The glass capillary tube 108 is connected at one end to a fluid supply (not shown) and at the other end has an orifice 102 generally in the range of about 0.5 to about 150 microns in diameter, and more preferably about 30 to about 60 microns. When a voltage is applied to the PZT actuator, the cross-section of the capillary glass tube 108 is reduced/increased producing pressure variations of the fluid enclosed in the glass capillary tube 108. These pressure variations propagate in the glass capillary tube 108 toward the orifice 102. The sudden change in cross-section (acoustic impedance) at the orifice 102, causes a drop to be formed. This mode of producing drops is generally called drop on demand (DOD).

In operation, the micro-jetting dispenser 100, depending on the viscosity and contact angle of the fluid, can require either positive or negative pressure at the fluid inlet 104. Typically, there are two ways to provide pressure at the fluid inlet 104. First, the pressure at the fluid inlet 104 can be provided by either a positive or a negative head by positioning of the fluid supply reservoir. For example, if the fluid reservoir is mounted only a few millimeters above the dispenser 100, a constant positive pressure will be provided. However, if the fluid reservoir is mounted a few millimeters below the dispenser 100, the orifice 102 will realize a negative pressure.

Alternatively, the pressure of the fluid at the inlet 104 may be regulated using existing compressed air or vacuum sources. For example, by inserting a pressure vacuum regulator between the fluid source and the dispenser 100, the pressure may be adjusted to provide a constant pressure flow to the dispenser 100.

In addition, a wide range of fluids including or containing beneficial agents may be dispensed through the dispenser 100. The fluids delivered by the dispenser 100 preferably have a viscosity of no greater than about 40 centipoise. The drop volume of the dispenser 100 is a function of the fluid, orifice 102 diameter, and actuator driving parameter (voltage and timing) and usually ranges from about 50 picoliters to about 200 picoliters per drop. If a continuous drop generation is desired, the fluid may be pressurized and a sinusoidal signal applied to the actuator to provide a continuous jetting of fluids. Depending on the beneficial agent dispensed, each drop may appear more like a filament.

It may be appreciated that other fluid dispensing devices may be used without departing from the present invention. In one exemplary embodiment, the dispenser is a piezoelectric micro-jetting device manufactured by MicroFab Technologies, Inc., of Plano, Tex. Other examples of dispensers will be discussed below with respect to FIGS. 7-9.

The electric cable 106 is preferably connected to associated drive electronics (not shown) for providing a pulsed electric signal. The electric cable 106 provides the electric signal to control the dispensing of the fluid through the dispenser 100 by causing the crystal to vibrate.

Figure 4:
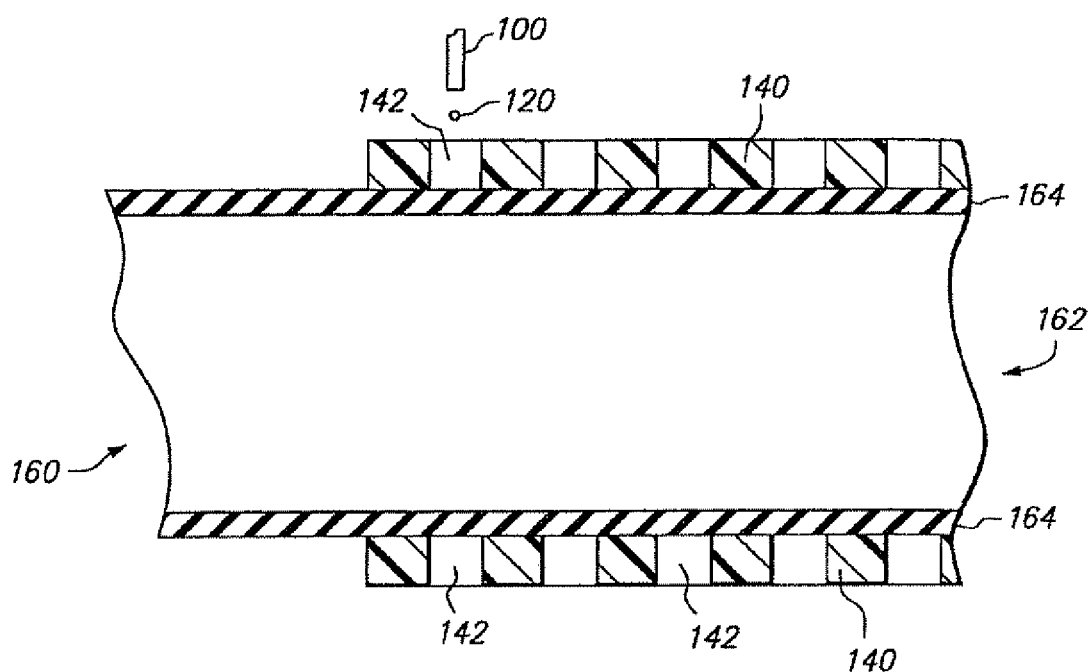
FIG. 4 is a cross-sectional view of an expandable medical device on a mandrel and a piezoelectric micro-jetting dispenser.

FIG. 4 shows an expandable medical device in the form of a stent 140 receiving a drop 120 of a beneficial agent from a piezoelectric micro-jetting dispenser 100. Into a hole 142. The stent 140 is preferably mounted to a mandrel 160. The stent 140 may be designed with large, non-deforming struts and links (as shown in FIG. 1), which comprise a plurality of openings 142 without compromising the mechanical properties of the struts or links, or the device as a whole. The openings 142 serve as large, protected reservoirs for delivering various beneficial agents to the device implantation site. The openings 142 may be circular, rectangular, or D-shaped in nature and form cylindrical, rectangular or D-shaped holes extending through the width of the stent 140. In addition, openings 142 having a depth less than the thickness of the stent 140 may also be used. It may be appreciated that other shaped holes 142 may be used without departing from the present invention.

The volume of the hole 142 will vary depending on the shape, depth and size of the hole 142. For example, a rectangular shaped opening 142 having a width of 0.1520 mm (0.006 inches) and a height of 0.1270 mm (0.005 inches) will have a volume of about 2.22 nanoliters. Meanwhile, a round opening having a radius of 0.0699 mm (0.00275 inches) will have a volume of about 1.87 nanoliters. A D-shaped opening having a width of 0.1520 mm (0.006 inches) along the straight portion of the D, has a volume of about 2.68 nanoliters. The openings according to one example are about 0.1346 mm (0.0053 inches) in depth having a slight conical shape due to laser cutting.

Although a tissue supporting device configuration has been illustrated in FIG. 1, which includes ductile hinges, it should be understood that the beneficial agent may be contained in openings in stents having a variety of designs including many of the known stents.

The mandrel 160 may include a wire member 162 encapsulated by an outer jacket 164 of a resilient or a rubber-like material. The wire member 162 may be formed from a metallic thread or wire having a circular cross-section. The metallic thread or wire is preferably selected from a group of metallic threads or wire, including Nitinol, stainless steel, tungsten, nickel, or other metals having similar characteristics and properties.

In one example, the wire member 162 has an outer diameter of between about 0.889 mm (0.035 inches) and about 0.991 mm (0.039 inches) for use with a cylindrical or implantable tubular device having an outer diameter of about 3 mm (0.118 inches) and an overall length of about 17 mm (0.669 inches). It can be appreciated that the outer diameter of the wire member 162 will vary depending on the size and shape of the expandable medical device 140.

Examples of rubber-like materials for the outer jacket 164 include silicone, polymeric materials, such as polyethylene, polypropylene, polyvinyl chloride (PVC), ethyl vinyl acetate (EVA), polyurethane, polyamides, polyethylene terephthalate (PET), and their mixtures and copolymers. However, it can be appreciated that other materials for the outer jacket 164 may be implemented, including those rubber-like materials known to those skilled in the art.

In one exemplary embodiment, the wire member 162 is encapsulated in a tubular outer jacket 164 having an inner diameter of about 0.635 mm (0.25 inches). The outer jacket 164 may be mounted over the wire member 162 by inflating the tubular member to increase to a size greater than the outer diameter of the wire member 162. The tubular member can be inflated using an air pressure device known to those skilled in the art. The wire member 162 is placed inside of the outer jacket 164 by floating the outer jacket 164 of silicon over the wire member 162. However, it may be appreciated that the wire member 162 may be encapsulated in an outer jacket of silicon or other rubber-like material by any method known to one skilled in the art.

In one exemplary embodiment for loading stents having a diameter of about 3 mm (0.118 inches) and a length of about 17 mm (0.669 inches), a wire member 162 having an outer diameter of 0.939 mm (0.037 inches) is selected. In one example, the wire member 162 is about 304.8 mm (12 inches) in length. The outer jacket 164 has an inner diameter of about 0.635 mm (0.025 inches).

The expandable medical device or stent 140 is then loaded onto the mandrel 160 in any method known to one skilled in the art. In one exemplary embodiment, the stents 140 and the mandrel 160 are dipped into a volume of lubricant to lubricate the stents 140 and the mandrel 160. The stents 140 are then loaded onto the mandrel 160. The drying of the stents 140 and the mandrel 160 create a substantially firm fit of the stents 140 onto the mandrel 160. Alternatively, or in addition to drying, the stents 140 may be crimped onto the mandrel 160 by a method known to one skilled in the art. The crimping ensures that the stents 140 will not move or rotate during mapping or filling of the openings.

Figure 5:
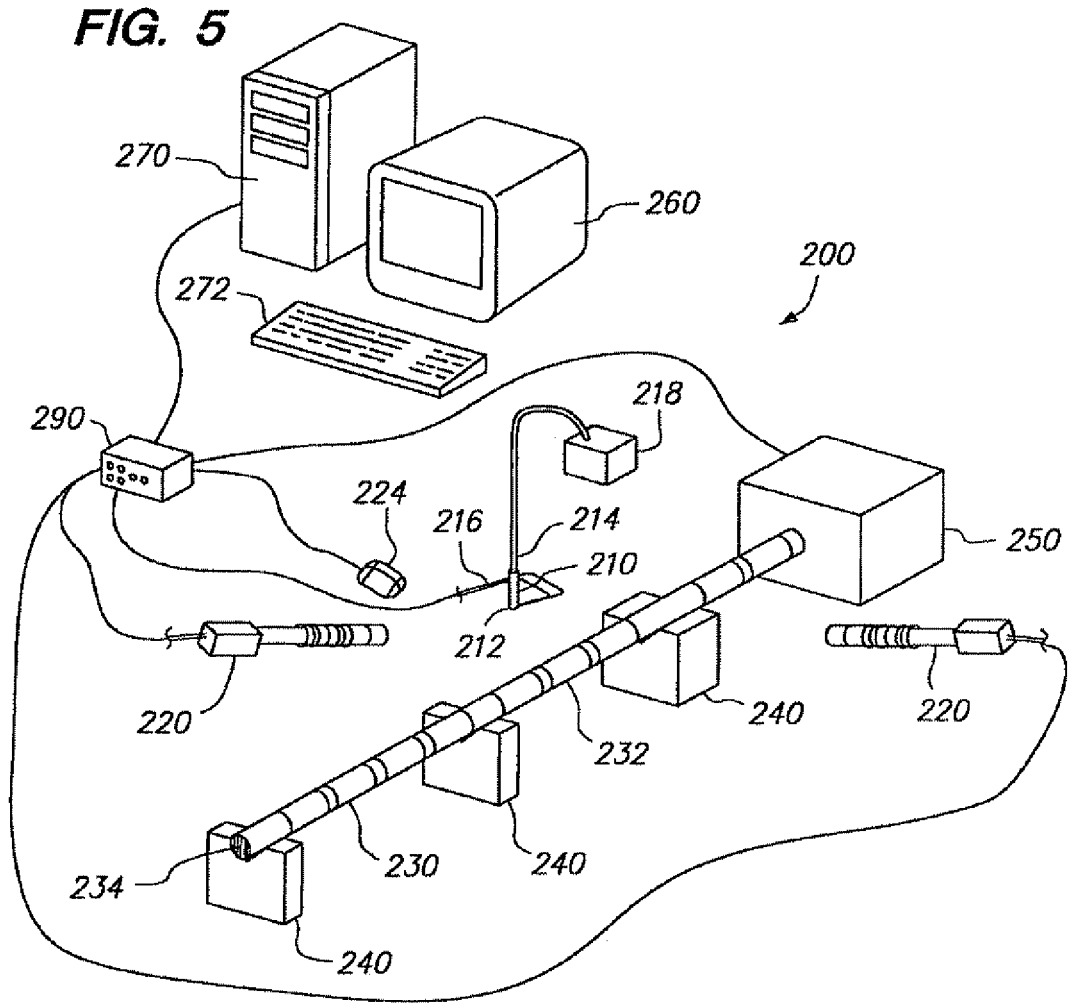
FIG. 5 is a perspective view of a system for loading an expandable medical device with a beneficial agent.

FIG. 5 shows a system 200 for loading a beneficial agent in an expandable medical device. The system 200 includes a dispenser 210 for dispensing a beneficial agent into an opening of an expandable medical device 232, a reservoir of beneficial agent 218, at least one observation system 220, and a mandrel 230 having a plurality of expandable medical devices 232 attached to the mandrel 230. The system 200 also includes a plurality of bearings 240 for supporting the rotating mandrel 230, a means 250 for rotating and translating the mandrel 230 along a cylindrical axis of the expandable medical device 232, a monitor 260, and a central processing unit (CPU) 270.

The dispenser 210 is preferably a piezoelectric dispenser for dispensing a beneficial agent into the opening in the medical device 232. The dispenser 210 has a fluid outlet or orifice 212, a fluid inlet 214 and an electrical cable 216. The piezoelectric dispenser 200 dispenses a fluid drop through the orifice 212.

At least one observation system 220 is used to observe the formation of the drops and the positioning of the dispenser 210 relative to the plurality of openings in the medical device 232. The observation system 220 may include a charge coupled device (CCD) camera. In one exemplary embodiment, at least two CCD cameras are used for the filling process. The first camera can be located above the micro-jetting dispenser 210 and observes the filling of the medical device 232. The first camera is also used for mapping of the mandrel 230 as will be described below. A second camera is preferably located on a side of the micro-jetting dispenser 210 and observes the micro-jetting dispenser 210 from a side or orthogonal view. The second camera is preferably used to visualize the micro-jetting dispenser during the positioning of the dispenser before loading of the medical device 232 with a beneficial agent. However, it can be appreciated that the observation system 220 can include any number of visualization systems including a camera, a microscope, a laser, machine vision system, or other known device to one skilled in the art. For example, refraction of a light beam can be used to count drops from the dispenser. The total magnification to the monitor should be in the range of 50 to 100 times.

In one exemplary embodiment, a LED synchronized light 224 with the PZT pulse provides lighting for the system 260. The delay between the PZT pulse and the LED pulse is adjustable, allowing the capture of the drop formation at different stages of development. The observation system 220 is also used in mapping of the mandrel 230 and medical devices 232 for loading of the openings. In one embodiment, rather than using a LED synchronized light 224, the lighting is performed using a diffused fluorescent lighting system. It may be appreciated that other lighting systems can be used without departing from the present invention.

A plurality of expandable medical devices 232 are mounted to the mandrel 230 as described above. For example, a mandrel which is about 12 inches in length can accommodate about 11 stents having a length of about 17 mm each. Each mandrel 230 is labeled with a bar code 234 to ensure that each mandrel is properly identified, mapped, and then filled to the desired specifications.

Figure 6:
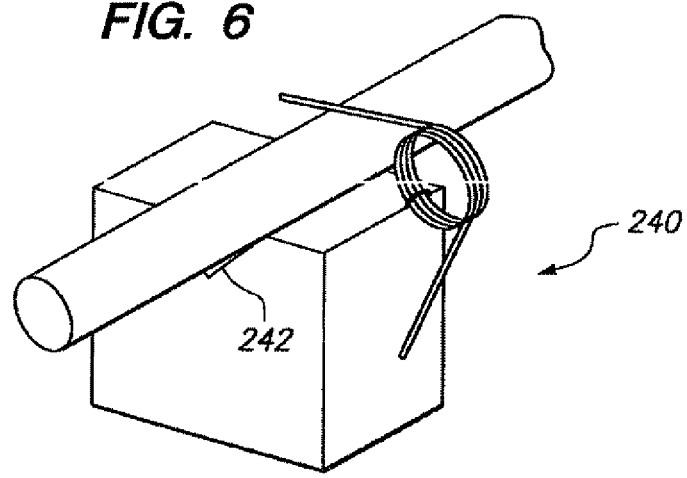
FIG. 6 is a perspective view of a bearing for use with the system of FIG. 5.

The mandrel 230 is positioned on a plurality of bearings 240. As shown in FIG. 6, one example of the bearings 240 have a V-shaped notch 242. The mandrel 230 is positioned within the V-shaped notch 242 and secured using a clip 244. The clip 244 is preferably a coil spring, however, other means of securing the mandrel within the V-shaped notch can be used including any type of clip or securing means can be used. The bearings 240 may be constructed of a metallic material, preferably different than the mandrel wire, such as stainless steel, copper, brass, or iron.

The mandrel 230 is connected to a means for rotating and translating the mandrel 250 along the cylindrical axis of the medical device 232. The means for rotating and translating the mandrel 250 can be any type or combination of motors or other systems known to one skilled in the art.

In one exemplary embodiment, the mandrel 250 and medical device 232 are moved from a first position to a second position to fill the openings of the medical device 232 with the beneficial agent. In an alternative exemplary embodiment, the system further includes a means for moving the dispensing system along the cylindrical axis of the medical device 232 from a first position to a second position.

A monitor 260 is preferably used to observe the loading of the medical device 232 with a beneficial agent. It can be appreciated that any type of monitor or other means of observing the mapping and loading process may be used.

A central processing unit 270 (or CPU) controls the loading of the medical device 232 with the beneficial agent. The CPU 270 provides processing of information on the medical device 232 for the dispensing of the beneficial agent. The CPU 270 is initially programmed with the manufacturing specifications as to the size, shape and arrangement of the openings in the medical device 232. A keyboard 272 is preferably used to assist with the loading of the CPU 270 and for input of information relating to the loading process.

The medical devices 232 are preferably affixed to the mandrel 230 and mapped prior to the loading process. The mapping process allows the observation system and associated control system to determine a precise location of each of the openings which may vary slightly from device to device and mandrel to mandrel due to inaccuracies of loading the devices on the mandrels. This precise location of each of the openings is then saved as the specific map for that specific mandrel. The mapping of the mandrel 230 is performed by using the observation system to ascertain the size, shape and arrangement of the openings of each medical device 232 located on the mandrel 230. Once the mandrel 230 including the plurality of medical devices 232 have been mapped, the mapping results are compared to the manufacturing specifications to provide adjustments for the dispenser to correctly dispense the beneficial agent into each of the holes of the medical device 232.

In an alternative exemplary embodiment, the mapping of the mandrel 230 is performed on an opening by opening comparison. In operation, the observation system maps a first opening in the medical device and compares the mapping result to the manufacturing specifications. If the first opening is positioned as specified by the manufacturing specifications, no adjustment is needed. However, if the first opening is not positioned as specified by the manufacturing specifications, an adjustment is recorded and an adjustment is made during the dispensing process to correct for the position which is different than as specified in the manufacturing specifications. The mapping is repeated for each opening of the medical device until each medical device 232 has been mapped. In addition, in one embodiment, if an opening is mapped and the opening is positioned pursuant to the manufacturing specifications, the mapping process can be designed to proceed to map at every other opening or to skip any number of openings without departing from the present invention.

After the mandrel has been mapped, the medical device 232 is filled with the beneficial agent based on the manufacturers' specification and adjustments from the mapping results. The CPU provides the programmed data for filling of each medical device 232. The programmed data includes the medical device design code, date created, lot number being created, number of medical devices 232 on the mandrel, volume of each opening in the medical device 232, different beneficial agents to be loaded or dispensed into the openings in the medical device 232, the number of layers, drying/baking time for each layer, and any other data.

In one exemplary embodiment, the medical device 232 will have at least 10 beneficial agent layers which will be filled including at least one barrier layer, at least one therapeutic layer having a beneficial agent, and at least one cap layer. The beneficial agent layers may include layers which vary in concentration and strength of each solution of drug or therapeutic agent, amount of polymer, and amount of solvent.

In operation, the operator will input or scan the bar code 234 of the mandrel into the CPU 270 before the filling process begins. The initial filling generally includes a mixture of polymer and solvent to create a barrier layer. Each of the openings are typically filled to about 80 percent capacity and then the mandrel with the medical device 232 still attached is removed from the system and placed into an oven for baking. The baking process evaporates the liquid portion or solvent from the openings leaving a solid layer. The mandrel is typically baked for about 60 minutes plus or minus 5 minutes at about 55 degrees C. To assist in error prevention, the CPU software receives the bar code of the mandrel and will not begin filling the second layer until at least 60 minutes since the last filling. The second layer and subsequent layers are then filled in the same manner as the first layer until the opening has been filled to the desired capacity. The reservoir 218 may also be bar coded to identify the solution in the reservoir.

The observation system 220 also may be utilized to verify that the dispenser 210 is dispensing the beneficial agent into the openings through either human observation on the monitor 270 or via data received from the observation system and conveyed to the CPU to confirm the dispensing of the beneficial agent in the openings of the medical device 232. Alternatively, refraction of a light beam can be used to count drops dispensed at a high speed.

The dispensers 100 run very consistently for hours at a time, but will drift from day to day. Also, any small change in the waveform will change the drop size. Therefore, the output of the dispenser 100 can be calibrated by firing a known quantity of drops into a cup and then measuring the amount of drug in the cup. Alternatively, the dispenser 100 may be fired into a cup of known volume and the number of drops required to exactly fill it may be counted.

In filling the openings of the medical device 232, the micro-jetting dispenser 100 dispenses a plurality of drops into the opening. In one preferred embodiment, the dispenser is capable of dispensing 3000 drops per second through a micro-jetting dispenser of about 40 microns. However, the drops are preferably dispensed at between about 8 to 20 shots per hole depending on the amount of fill required. The micro-jetting dispenser fills each hole (or the holes desired) by proceeding along the horizontal axis of the medical device 232. The CPU 270 turns the dispenser 100 on and off to fill the openings substantially without dispensing liquid between openings on the medical device. Once the dispenser has reached an end of the medical device 232, the means for rotating the mandrel rotates the mandrel and a second passing of the medical device 232 along the horizontal axis is performed. In one embodiment, the medical devices 232 are stents having a diameter of about 3 mm and a length of about 17 mm and can be filled in about six passes. Once the medical device 232 is filled, the dispenser 210 moves to the next medical device 232 which is filled in the same manner.

The CPU 270 insures that the mandrel is filled accurately by having safety factors built into the filling process. It has also been shown that by filling the openings utilizing a micro-jetting dispenser, the amount of drugs or therapeutic agent used is substantially less than coating the medical device 232 using previously known method including spraying or dipping. In addition, the micro-jetting of a beneficial agent provides an improved work environment by exposing the worker to a substantially smaller quantity of drugs than by other known methods.

The system 200 also includes an electrical power source 290 which provides electricity to the piezoelectric micro-jetting dispenser 210.

The medical devices 232 may be removed from the mandrel by expanding the devices and sliding them off the mandrel. In one example, stents may be removed from the mandrel by injecting a volume of air between the outer diameter of the wire member 162 and the inner diameter of the outer jacket. The air pressure causes the medical device 232 to expand such that the inner diameter of the medical device 232 is greater than the outer diameter of the mandrel. In one embodiment, a die is place around the mandrel to limit the expansion of the medical device 232 as the air pressure between the outer diameter of the wire member 162 and the inner diameter of the outer jacket 164. The die can be constructed of stainless steel or plastics such that the medical devices 232 are not damaged during removal from the mandrel. In addition, in a preferred embodiment, the medical devices 232 are removed four at a time from the mandrel. A 12-inch mandrel will accommodate about 11, 3 mm by 17 mm medical devices having approximately 597 openings.

FIG. 7 illustrates one exemplary embodiment of a dispenser 300 which precisely delivers drops by acoustic drop ejection. The dispenser 300 includes an acoustic energy transducer 310 in combination with a replaceable fluid reservoir 320. The dispenser 300 releases a nanoliter or picoliter drop from a surface of the liquid in the reservoir 320 accurately into an opening in the medical device 140 positioned in the path of the drop.

The dispenser 300 operates by focusing acoustic energy from the transducer 310 through a lens onto the surface of the fluid in the reservoir 320. The fluid then creates a mound at the surface which erupts and releases a drop of a controlled size and trajectory. One example of a system for focusing the acoustic energy is described in U.S. Pat. No.

6,548,308 which is incorporated herein by reference. The medical device 140 and mandrel 164 may be moved or the dispenser 300 may be moved to precisely control the dispensing of the drops into the openings in the medical device.

Some of the advantages of the use of an acoustic dispenser 300 include the ability to deliver more viscous fluids and the ability to deliver volatile fluids containing solvents. For example, the fluids delivered by the dispenser 300 can have a viscosity of greater than about 40 centipoise. The delivery of more viscous materials allows the use of higher solids content in the delivered fluid and thus, fewer layers. The drop volume when using the dispenser 300 is a function of the fluid and transducer driving parameters and can range from about 1 picoliter to about 50 nanoliters per drop.

The dispenser 300 also has the advantage of simple and fast transfer between dispensed liquids since the reservoir is self contained and the parts do not require cleaning. In addition, no loss of drug occurs when switching between drugs.

The acoustic dispenser 300 delivers the drop in a straight trajectory without any interference from the side walls of the reservoir 320. The straight trajectory of the fluid drops allows the dispenser 300 to operate accurately spaced away from the medical device to allow improved visualization.

FIG. 8 illustrates an alternate exemplary embodiment of a reservoir 400 for an acoustic dispenser which may deliver compositions containing volatile solvents. The reservoir 400 includes a vapor chamber 410 above the fluid chamber 420. The vapor chamber 410 retains evaporated solvent vapor and reduces the rapid evaporation rate of the volatile solvents by providing a high concentration of solvent vapor at the surface of the liquid.

The dispenser 500 of FIG. 9 uses a solvent cloud formation system to surround a dispenser 510, such as the piezoelectric dispenser of FIG. 3, with a cloud of the same solvent used in the dispensed fluid to reduce solvent evaporation and fowling of the dispenser tip. In the FIG. 9 example, the solvent cloud is created by a ring 520 of porous material, such as porous metal, through which the solvent is delivered by a feed line 530 from an auxiliary solvent source. The solvent evaporating from the porous material ring 520 creates a cloud of solvent directly around the dispenser tip. The creation of a solvent cloud around a dispenser tip reduces the solvent vapor concentration differential near the tip of the dispenser. Lowering this differential will increase the time that the dispenser may be left idle without clogging due to solvent evaporation. This improves the robustness of the process.

Alternatively, or in addition to the solvent cloud formation system shown in FIG. 9, other gases may be delivered to form a cloud or controlled local environment around the tip of the dispenser which assists in dispensing and reduces clogging of the dispenser.

The gas delivered around the dispenser tip, called a shield gas, creates a desirable local environment and shields the dispenser tip and the dispensed fluid from gases which can be detrimental to the dispensing process. Systems for delivering shield gases are known in the fields of welding and laser cutting and can include one or more outlets, jets, or nozzles positioned close to the dispensing tip for creating a desired local environment at the processing location. The term shield gas as used herein refers to a gas delivered locally around a work area to change the local environment.

In one example, a shield gas is used with a biologic agent, such as cells, genetic material, enzymes, ribosomes, or viruses. The shield gas can include a low oxygen gas creating a reducing atmosphere used to prevent oxidation.

In another example, the presence of high humidity in the environment increases the water content in the liquid solution dispensed by the dispenser tip. The high water content caused by high humidity can cause some drugs to crystallize and clog the dispenser tip. This clogging due to humidity is particularly seen where a lipophilic agent, such as one or more of the drugs paclitaxel, rapamycin, everolimus, and other limus drugs, is dispensed. Thus, a dry shield gas may be used to prevent clogging. In addition, the use of one or more solvents in the dispensed fluid that absorb water from a high humidity environment may stimulate the crystallization of the drugs caused by high humidity. For example, the solvent DMSO absorbs water in a high humidity environment and increases the precipitation and crystallization of some agents. The humidity within the local environment surrounding the dispensing tip may be controlled to provide a desired humidity level depending on the particular beneficial agent combination used, for example, the local humidity can be maintained below 45 percent, below 30 percent, or below 15 percent.

Examples of dry gases which may be used as the shield gas include nitrogen; inert gases, such as argon or helium; dry air; or a combination thereof. The term dry gas as used herein means a gas having a water content of less than 10 percent, and preferably a dry gas selected has less than 1 percent water content.

The shield gas may be provided in a pressurized liquid form which is expanded and vaporized when delivered as the shield gas. Alternately, a shield gas may be stored in a gaseous form or created by removal of water from air or another gas. The shield gas orifice for delivery of the shield gas should be positioned close to the dispenser tip, for example within about 1 inch, preferably within about 1/4 inch from the dispensing tip. The dispensing tip may also be surrounded on two or more sides by shields or shrouds which contain the shield gas creating a local environment between the shields and surrounding the dispensing tip.

The shield gas dispensing system may be controlled based on a sensed condition of the environment. For example, the shield gas flow rate may be automatically controlled based on a humidity of the room or a local humidity near the dispensing tip. Alternately, the shield gas may be automatically activated (turned on or off) by a local humidity sensor which senses a humidity near the dispensing tip or an in room humidity sensor. The shield gas dispensing system may also be controlled based on other sensed conditions of the environment, such as oxygen content.

The shield gas dispensing system may substantially reduce clogging of the dispensing tip, particularly of a piezoelectric dispensing tip by controlling the local environment around the dispensing tip. This shield gas may eliminate the need for careful control of environmental conditions of the entire room. The system may economically prevent clogging of the dispenser due to different clogging mechanisms including crystallization of agents, rapid evaporation of solvents, drying, and others.

In the example below, the following abbreviations have the following meanings. If an abbreviation is not defined, it has its generally accepted meaning.

TABLE I

| Solutions | Drug | Polymer | Solvent |
|---|---|---|---|
| A | None | 4% PLGA DMSO 50/50 | DMSO |
| DA | 0.64% paclitaxel | 8% PLGA 50/50 | DMSO |

TABLE I-continued

| Solutions | Drug | Polymer | Solvent |
|---|---|---|---|
| DD | 0.14% paclitaxel | 8% PLGA 50/50 IV = 0.60 IV = 0.59 | DMSO |
| L | None | 8% PLGA 50/50 IV = 0.59 | DMSO |

DMSO = Dimethyl Sulfoxide
IV = Inherent Viscosity
PLGA = poly(lactide-co-glycolide)

TABLE II

| Layer No. | Solution | Layer No., this Solution |
|---|---|---|
| 1 | A | 1 |
| 2 | A | 2 |
| 3 | A | 3 |
| 4 | A | 4 |
| 5 | A | 5 |
| 6 | A | 6 |
| 7 | A | 7 |
| 8 | A | 8 |
| 9 | A | 9 |
| 10 | DA | 1 |
| 11 | DA | 2 |
| 12 | DD | 1 |
| 13 | L | 1 |

A plurality of medical devices, preferably 11 medical devices per mandrel are placed onto a series of mandrels. Each mandrel is bar coded with a unique indicia which identifies at least the type of medical device, the layers of beneficial agents to be loaded into the opening of the medical devices, and a specific identity for each mandrel. The bar code information and the mapping results are stored in the CPU for loading of the stent.

A first mixture of poly(latide-co-glycolide) (PLGA) (Birmingham Polymers, Inc.), and a suitable solvent, such as DMSO is prepared. The mixture is loaded by drops into holes in the stent. The stent is then preferably baked at a temperature of 55 degrees C. for about 60 minutes to evaporate the solvent to form a barrier layer. A second layer is laid over the first by the same method of filling polymer solution into the opening followed by solvent evaporation. The process is continued until 9 individual layers have been loaded into the openings of the medical device to form the barrier layer.

A second mixture of paclitaxel, PLGA, and a suitable solvent such as DMSO forming a therapeutic layer is then introduced into the openings of the medical device over the barrier layer. The solvent is evaporated to form a drug filled device protective layer and the filling and evaporation procedure repeated until the hole is filled until the desired amount of paclitaxel has been added to the openings of the medical device.

A third mixture of PLGA and DMSO is then introduced into the openings over the therapeutic agent to form a cap layer. The solvent is evaporated and the filling and evaporation procedure repeated until the cap layer has been added to the medical device, in this embodiment, a single cap layer has been added.

In order to provide a plurality of layers of beneficial agents having a desired solution, the reservoir is replaced and the piezoelectric micro-jetting dispenser is cleaned. The replacement of the reservoir and cleaning of the dispenser (if necessary) insures that the different beneficial layers have a desired solution including the correct amount of drugs, solvent, and polymer.

Following implantation of the filled medical device in vivo, the PLGA polymer degrades via hydrolysis and the paclitaxel is released.

As inkjet printing technology is increasingly applied in a broader array of applications, careful characterization of its method of use is critical due to its inherent sensitivity. A common operational mode in inkjet technology known as drop-on-demand ejection is used as a way to deliver a controlled quantity of material to a precise location on a target. This method of operation allows for the ejection of individual or the ejection of a sequence (burst) of drops based on a timed trigger event. The present invention describes an examination of sequences of drops as they are ejected, indicating a number of phenomena that must be considered when designing a drop-on-demand inkjet system. These phenomena appear to be driven by differences between the first ejected drop in a burst and those that follow it and result in a break-down of the linear relationship expected between driving amplitude and drop mass. This first drop, as quantified by high-speed videography and subsequent image analysis, detailed below, may be different in morphology, trajectory, velocity and volume from subsequent drops within a burst. These findings were confirmed orthogonally by both volume and mass measurement techniques which allowed for quantization down to single drops.

In an increasingly broad spectrum of applications, the ability to accurately and repeatedly deliver nanogram quantities of a given substance to a precise target location is critical to the development of new technologies. While inkjet technology is most commonly associated with printing applications, it has recently been utilized in a number of other areas, including the manufacturing of medical devices for the deposition of solutions containing polymers, drugs or combinations of the two.

Figure 10:
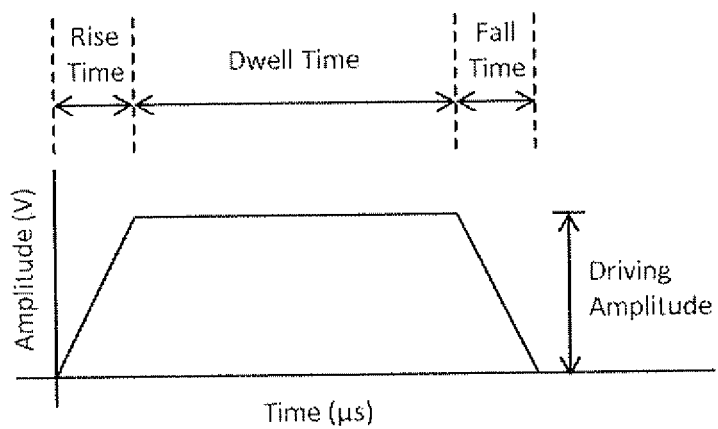
FIG. 10 is a diagrammatic representation of an exemplary waveform for controlling an inkjet dispenser with input parameters labeled in accordance with the present invention.

Inkjet technology is based on acoustic principles and has been described in great detail previously. The typical inkjet dispenser comprises a hollow glass tube with a piezoelectric element surrounding its outer diameter. This piezoelectric element is dimensionally perturbed by increasing and decreasing driving amplitudes, which expand and contract its diameter, respectively. These expansions and contractions produce pressure waves within the glass tube which, in the correct combination and timing, result in drop ejection. A typical driving waveform is illustrated in FIG. 10 with the relevant parameters labeled. Typical parameters for the solution utilized herein were a 3 micro second rise time, a 20 micro second dwell time, a 3 micro second fall time and a 26 volt amplitude driver at a frequency of 2.8 kHz. While all of these parameters will have some impact on drop mass, driving amplitude is the dominant factor and is thus the primary control mechanism of ejected mass.

Electrical parameters are just one subset of the factors that will determine ejected drop size and morphology; others include orifice size and condition, fluid properties, fluidic head and environmental factors. These factors, which are not of primary concern for this work, were controlled as closely as possible to avoid confounding effects.

Inkjet technology may be implemented in two main operational modes; namely, continuous and drop-on-demand. In continuous operation, drive electronics provide a constant set of driving waveforms, resulting in drops that are dispensed continuously at a fixed frequency. Because it may be undesirable for all of these drops to reach the target, the drops are often charged via an electrostatic field and then deflected using another field to control their trajectory. In this way, the number of drops that reach the target may be controlled through fluctuations in the electric field.

Since the inclusion of these systems significantly increases their complexity and cost, many applications choose instead to operate inkjets in the drop-on-demand mode. In this mode, drive electronics only deliver a set number of drive waveforms upon triggering, resulting in a controllable number of drops reaching the target. This sequence of drops may then be triggered to dispense only when the desired target location is in position, eliminating the need to deflect unwanted drops. Many applications use this method to deliver small quantities of drops to various points along a target surface, such as solder points in electronic circuits and reservoirs in drug-eluting stents as described herein. The number of drops dispensed at each trigger event may be modified to control the final amount of substance that is dispensed and may even be adjusted in real-time in a closed-loop controlled system to account for process drift or sudden changes in ejected mass.

To control the total amount of material delivered to the target, drop-on-demand operation allows for adjustment of drop size as well as the number of drops delivered per trigger. However, there has been very limited work conducted to characterize how changes to the number of drops delivered per burst might affect ejection behavior. Using drop number as a control for the quantity of material delivered to locations along a target assumes that each drop is equal in mass, implying a linear relationship between quantity of drops and total ejected mass. The present invention challenges this assumption and shows how, specifically, the first ejected drop may be different in both quality and quantity from those that come after it, resulting in a non-linear response between number of drops in a burst and ejected mass. This difference is also affected by the driving waveform, adding another layer of complexity to drop-on-demand inkjets that must be taken into account when designing such a system.

Figure 11:
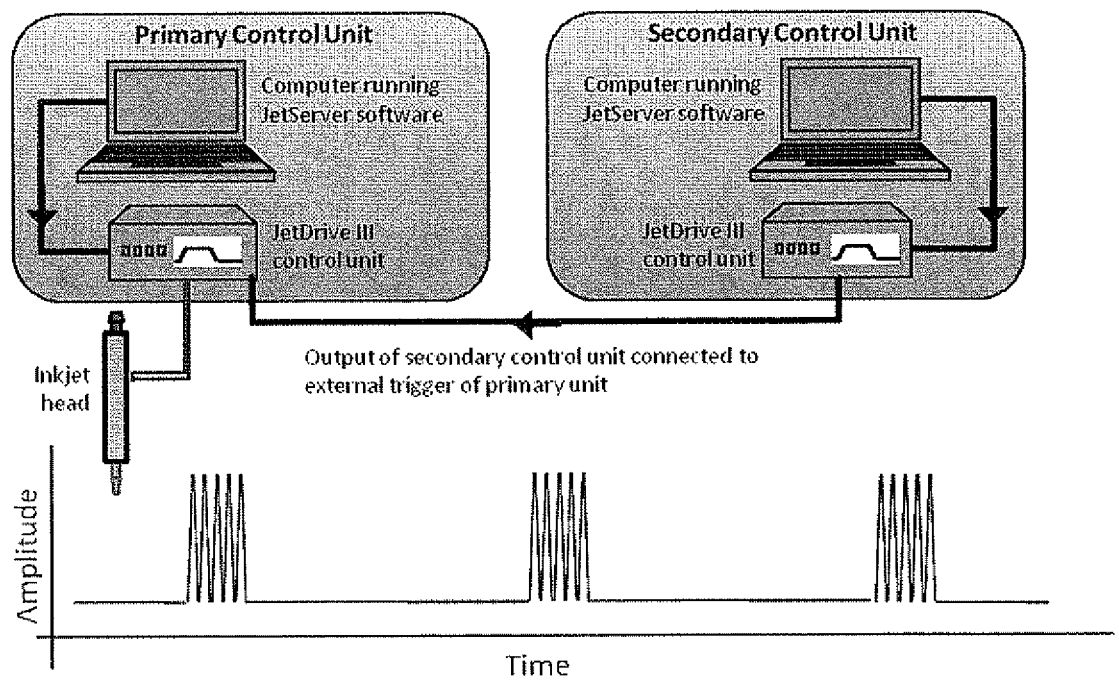
FIG. 11 is a diagrammatic representation of the electronics required to dispense a desired number of sequences of drops in accordance with the present invention.

A commercially-available drop-on-demand inkjet system from MicroFab Technologies was employed in the study described herein. The inkjet head was a low-temperature unit with a 40 µm orifice diameter (MicroFab MJ-AB-63-40, MicroFab Technologies, Plano, Tex.) and was driven using a JetDrive III electronics control unit, which was connected to a standard computer running the JetServer software. Since triggering through the JetServer software is limited by bus rates and software-related cycle times to approximately 250 ms, two JetDrive units were connected in a cascading configuration. In this way, the first control unit was used to set the driving waveform parameters for drop ejection as well as the number of drops required per burst, while the second unit controlled the number of bursts to be dispensed, as well as the interval between them. This is described pictorially in FIG. 11 along with an example of a resulting set of waveforms. As illustrated in FIG. 11, a secondary control unit is used to trigger a primary control unit, which is connected directly to the inkjet head.

The liquid used in these experiments was a solution of drug and polymer dissolved in dimethyl sulfoxide (DMSO) as used in filling of NEVO™ Sirolimus-eluting coronary stents. The addition of polymer resulted in a non-Newtonian fluid behavior. In order to reduce the viscosity of the solution enough to allow for consistent dispensing, the solution was heated to 40 degrees C. as it passed through the inkjet unit, reducing the viscosity to 4.95 cP and the surface tension to 41.5 dyn/cm. The solution vial was kept vented to atmospheric pressure and the solution level was maintained at the same height as the tip of the inkjet to ensure a consistent static fluid head.

A common underlying problem with inkjet dispensers of this type is solvent evaporation at the dispenser orifice potentially causing blockages at the jet tip as the solids in the solution precipitate out of solution. For the solution used in these studies, evaporation effects were minimal due to the relatively high boiling point of DMSO (189 degrees C.). However, DMSO is also highly hygroscopic and so water absorption was of greater concern than solvent evaporation due to the ambient humidity conditions present during experimentation (approximately 30 percent). The net effect at the jet tip for either solvent evaporation or water absorption remains the same, though, as both of these could drive the dissolved polymer and drug to precipitate, resulting in potential orifice blockages. To avert water absorption, nitrogen gas (99.998 percent high purity grade, Airgas, Inc., Radnor, Pa.) was kept continuously flowing around the orifice of the inkjet at 1.0 L/min to exclude moisture from this area.

A combination of methods was used for the following experimentation, each providing a different means of quantifying differences between drops in a sequence. Initial work was performed by image analysis using pictures captured by a high-speed video camera (Phantom v9.1, Vision Research, Inc., Wayne, N.J.) with drops illuminated from behind using a standard projection-bulb lighting source. Images of drop sequences were recorded at a frame rate matching the ejection frequency (2.8 kHz) to capture one frame per drop. These images were then analyzed using the ImageJ image-analysis software suite (National Institutes of Health, Bethesda, Md.). Drop volume was determined by first performing a threshold function on the image and then measuring the diameter of the drop, from which the volume could be calculated. The camera and lens system was calibrated using an N.I.S.T. traceable optical standard from Edmund Optics (Barrington, N.J.). Images were recorded at a sufficient distance from the jet tip to allow vibrations in the drop caused by Plateau-Rayleigh instability to be damped (approximately 1 mm) to maximize sphericitiy.

More sensitive drop mass quantification was carried out by means of UV spectroscopy. In this method, a number of drops (between 1 and 5) were dispensed into 100 µL of MilliQ de-gassed de-ionized water and then transferred by pipette to an Agilent quartz Ultra-micro 10 mm path length cuvette. These samples were analyzed for absorption at 208 nm, an absorbance peak associated with DMSO, from which the concentration of DMSO, and subsequently drop volume, could be calculated through a predetermined standard curve. While this method's repeatability (4.1 percent RSD for 1 to 5 drops) could not match that of weighing larger numbers of drops (0.26 percent RSD at 200 drops), it provided superior sensitivity for small drop counts.

The final method employed was to dispense a larger number of drops into a small weighing vessel (VWR Aluminum Micro Weighing Dishes). This vessel was then weighed on a Mettler-Toledo UMX2 sub-microgram balance immediately after capture to limit solvent evaporation and moisture absorption. Both of these potentially mitigating factors were experimentally measured and determined to be sufficiently low to allow for accurate measurements. Due to the limits of this balance, this method required a larger quantity of drops to be dispensed (greater than 1000 drops) to provide adequate precision (repeatability of 0.26 percent RSD at 2000 drops).

These methods were used in combination to analyze various aspects of the effect of first drop dissimilarities on jet performance. High-speed videography provided qualitative assessments of drop morphology as well as trajectory and velocity measurements, UV spectroscopy provided precise quantization of small volumes of liquid (down to single drops on the order of 90 pL) and mass determination by microbalance provided rapid analysis of large sample sizes while maintaining adequate precision.

The combination of methods described above allowed for careful analysis of inkjet performance in drop-on-demand scenarios. Inkjets operated in this mode deliver bursts of drops separated by a controllable time interval, which is useful for delivering more than one drop to different points along a target. In this study, individual drops within these bursts were analyzed for morphology, trajectory, velocity and volume to determine how differences between them might affect ejection behavior. Sequences of drops were analyzed in this way for morphology, trajectory, velocity and volume with specific attention to how these were different within a sequence.

Figure 12:
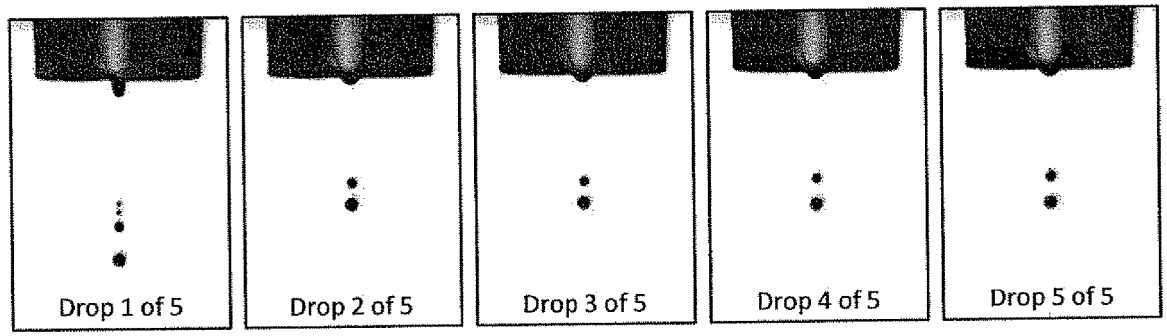
FIG. 12 are high speed images captured with a shutter speed of 2 microseconds at a rate of 2,800 fps showing the dissimilarity between drops in a sequence in accordance with the present invention.

Images captured by high-speed videography were the first indication that ejection of this solution did not yield identical drops when dispensed in a burst. An example of a burst of 5 drops is illustrated in FIG. 12, which demonstrates the dissimilarity in morphology and velocity. These images were captured with a shutter speed of 2 micro seconds at a rate of 2800 fps and illustrate the dissimilarity between drops in a sequence. The first drop is travelling faster as evidenced by its distance from one jet tip relative to the later drops and has a trail of small satellite drops tailing it which is inconsistent with the morphology of later drops. While these attributes are very consistent for drops 2 through 5, the first drop does not match this behavior, exhibiting higher ejection velocity and a tail of smaller satellite drops. Long tails of satellite drops are undesirable from a targeting perspective and may also contribute to variability in ejected mass.

Figure 13:
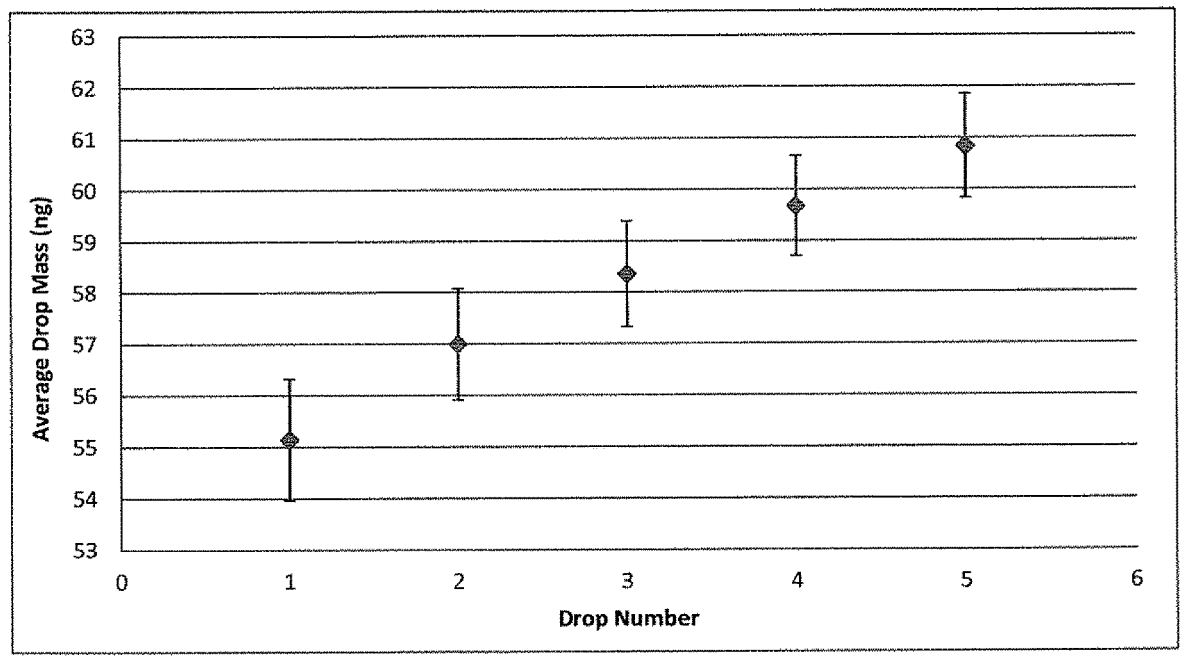
FIG. 13 is a plot of the results of image analysis for high speed videography of 25 sets of bursts of 5 drops with adjacent bursts separated by 30 microseconds in accordance with the present invention.

Image analysis provided quantization of drop volume for a large set of images such as those shown above. High-speed video was collected for 25 sequences as described and illustrated herein and analyzed for mean drop mass, with the results illustrated in FIG. 13. Specifically, image analysis for high speed videography of 25 sets of bursts of 5 drops, with adjacent bursts separated by 30 ms was performed. Edge detection was performed to determine drop diameter from which drop mass was calculated. Mean and two standard derivations are shown. For this particular set of driving conditions (dwell time=23 μs, amplitude=20 V), drop mass was found to increase with order of ejection, with the fifth drop 10.3±2.2 percent larger than the first. Due to this effect, bursts of drops ejected in this manner would exhibit increasing average drop mass as a function of quantity of drops in a burst, resulting in the requirement for additional jet calibration activities to accurately predict ejected mass.

In order to eliminate the possibility that solution effects were driving this phenomenon, limiting its applicability to the liquid used in these studies, high-speed videography was repeated with a pure solvent, in this case de-ionized water (driving parameters of 18 μs dwell time, 12 V amplitude). While these images are not illustrated, similar behavior was observed with the first in a burst of drops exhibiting increased velocity as well as morphology inconsistent with those that followed it. Therefore, this behavior must not be a result of the non-Newtonian behavior of the polymer solution and a more fundamental effect present during ejection of various fluids.

While gravimetric measurements by microbalance were only useful for numbers of drops above 1000, it did provide an efficient way to measure a large numbers of samples. In these studies, the average drop weight was determined by accumulating sufficient drops for precise measurement using large sets of bursts and varying the number of drops per burst. Shown in FIG. 14 is one example of this, plotting average drop mass as a function of driving amplitude for 5 and 800 drops per burst. While the larger drop number demonstrates excellent linearity the smaller number shows a non-linear behavior, with low and high amplitudes having the same slope but different from each other, Regions A and C respectively, with a middle transition region, Region B. While this behavior has routinely been reported to be linear, this plot clearly indicates that this is not always the case. For the liquid used in these studies, smaller drop sequences display a non-linear behavior with three distinct regimes within this amplitude range: low (Region A) and high (Region C) amplitudes have the same slope but different intercepts while a transition zone (Region B) between these has a different slope and intercept.

This non-linearity is critical for applications in which the calibration of an inkjet device needs to be highly accurate (e.g. delivery of an active pharmaceutical ingredient). Under some circumstances, it may be attractive from a process design standpoint to calibrate an inkjet device by dispensing a large number of drops in one sequence instead of in smaller, more process-reflective bursts, for instance for improved calibration precision or to reduce calibration time. However, this data indicates that this is not always an appropriate solution, as average drop mass will change with the number of drops dispensed per burst. Thus, a truly accurate calibration may only be achieved by dispensing the same number of drops per burst as used in the actual process.

Because these curves intersect at one particular driving amplitude, one might also consider operating the inkjet at this setting and not taking this effect into account. However, it should be noted that for this liquid, this transition region did not occur at the same amplitude over a period of days. That is, the amplitude at which these curves intersected changed +/−2 volts over a period of a week. The cause of this is not clear; however, from a practical standpoint, this relationship would have to be re-established at appropriate time intervals in order to ensure that this cross-over amplitude has not changed.

In order to understand the effects driving this behavior, it was necessary to repeat the high-speed videography described above for driving amplitudes above the transition zone. This was not feasible, however, since drop morphologies were highly irregular at these amplitudes with non-spherical drop morphologies and many satellite drops. Because of this, image analysis was not able to produce sufficiently accurate results. Instead, results were obtained gravimetrically by determining average drop mass as a function of drops per burst. In order to achieve this, the same total number of drops was dispensed, in this case 1800, but with different numbers of drops in each burst.

The results are illustrated in FIG. 15 which is a plot of average drop mass as a function of quantity of drops in a burst. The resulting average drop mass behavior illustrates the dissimilarity of the first drop from those that follow. Inkjet parameters were given as 18 micro seconds dwell time, 38 v amplitude and 2.8 kHz driving frequency with a 30 ms delay between sequences. Error bars indicate two standard deviations. These results, illustrated in FIG. 15 appear to contradict the high-speed videographic data presented in FIG. 13. However, this study was performed with different inkjet parameters, such that it was operating above the transition zone (Region C) identified in FIG. 14. As a result, the first drop is now shown to have significantly higher mass than subsequent drops whereas at lower amplitudes (Region A) it had lower mass (see FIG. 13). As a result of this first drop dissimilarity, small and large burst sizes produced at the same driving amplitude would be expected to demonstrate different average drop masses since small bursts would be heavily influenced by the first drop while large enough sets would mask this effect.

This finding, then, corroborates the data presented in FIG. 14. With large sets of drops, drop weight changes linearly with driving amplitude since this set is large enough to overcome the effect of the first drop. However, smaller sets show much more sensitivity to this effect. Further, the mass of the first drop is also very sensitive to driving amplitude, much more so than later drops in a sequence. As a result, the first drop is smaller than subsequent drops for low amplitudes and larger for high amplitudes. This, then, produces the non-linear behavior described above.

While the microbalance measurements above seemed to identify the phenomenon driving this effect, there was no direct measurement of individual drop mass and so confounding effects, such as different heat transfer profiles to the jet over the sample collection time (potentially caused by different bulk mass flow rates due to the varying number of drops in a burst) could have been introduced. A confirmatory study was therefore performed using UV spectroscopy, which was sensitive enough to quantify single drops. This method allowed for accurate quantization of single bursts of drops instead of larger multiple of them, as required for gravimetric measurements.

Figure 16:
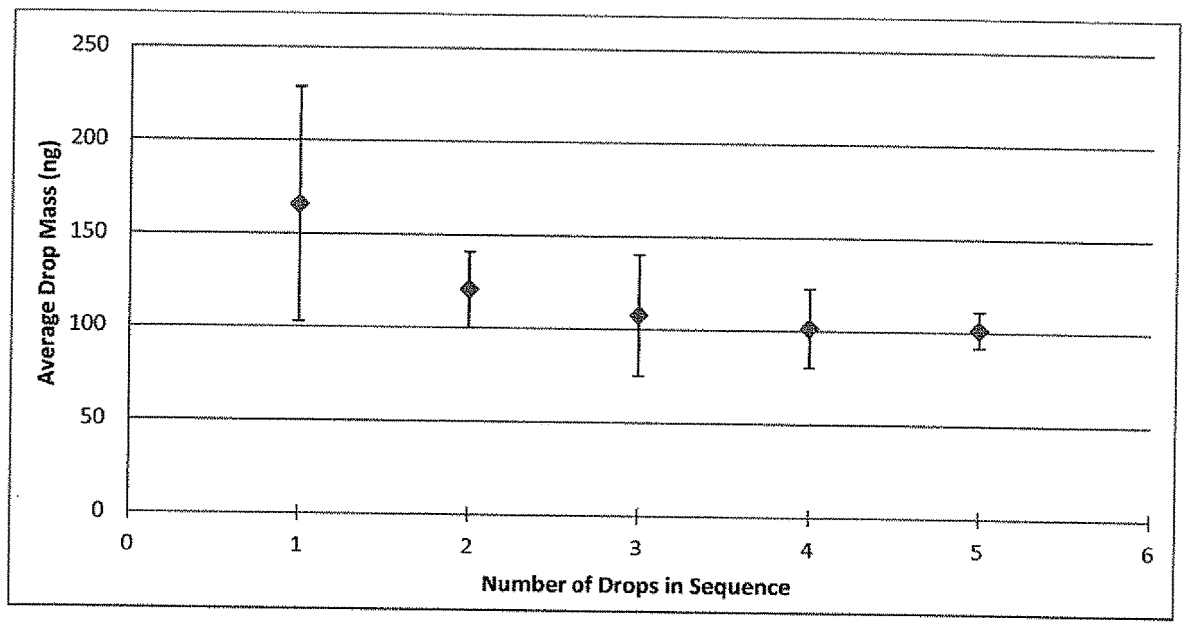
FIG. 16 is a plot of the average mass per drop for sequences of varying drop numbers in Region C as defined in FIG. 14 in accordance with the present invention.

While the repeatability of the UV method to measure the mass of small quantities of drops (1 to 10) was not as robust as the gravimetric method (which required close to 2,000 drops), the sensitivity of the UV method allowed for mass determinations of single drops, allowing for verification of trends seen in other methods without confounding factors. In this case, as illustrated in FIG. 16 with the jet operating in Region C of FIG. 14, these data support earlier results, indicating that the average mass of the first drop in a sequence is larger than later drops with the average drop mass leveling out around the third drop. Absorbance spectra were analyzed at 208 nano meters after subtracting water blank to detect DMSO. Mass was calculated from concentration which was determined through a standard curve from absorbance data. Mean values of 10 samples and two standard deviations are shown in FIG. 16.

Previous studies have indicated the existence of what is often termed the "first drop problem," but this appears to be a phenomenon of a different time scale than what is presented herein. The commonly-referenced first drop problem refers to clogging or misfiring of an inkjet due to solvent evaporation at the orifice. Depending on the solvent utilized, this effect would take on the order of seconds or minutes to present itself at a level significant enough to have this kind of impact. However, the current effect is seen in every sequences of drops with only a 30 ms interval between them, indicating a phenomenon beyond solvent evaporation or, more relevant to the current scenario, water absorption. This effect, then, is hypothesized to be caused by a combination of effects including a) acoustic instability in the channel of the inkjet, a result of insufficient time for regular acoustic reverberations to establish themselves within this channel, and b) orifice wetting effects, a result of fluid build-up around the jet orifice, which would occur only after drops begin to be dispensed. In the case of the unstable acoustics, after the 30 ms interval between bursts, these acoustic reverberations would be sufficiently damped for this first drop phenomenon to reestablish itself, resulting in its observation in every burst of drops. A similar explanation would follow for the surface wetting case: a 30 ms delay would be sufficient to allow liquid that had collected around the orifice during ejection to be drawn back into the inkjet channel, leading to its repetition at the beginning of each burst. Attempts to limit solvent evaporation, as has been suggested elsewhere, would not ameliorate either of these problems, as evidenced by this effect's presence even during ejection of pure water.

Drop-on-demand operation of inkjet devices provides a simple way to precisely control the quantity of material reaching a target. However, it has been shown here that significantly more characterization is required to implement drop-on-demand dispensing than continuous dispensing operations. This is largely a result of the dissimilarity between the first drop ejected and subsequent drops, where the first drop is often different in morphology and trajectory, both of which would affect the ability to accurately reach the target, as well as in mass, which would impact dispensing accuracy. This will be of greatest concern to applications in which small quantities of drops are the deposited on various points along a target, as it is small drop bursts that are most sensitive to effects introduced by the first drop. Because the size of the first drop relative to those that follow is a function of driving amplitude, neither the direction nor the magnitude of the bias introduced by this effect will be consistent and, thus, cannot be accounted for mathematically. While deflecting this first drop to prevent it from reaching the target would be the ideal solution, in practice this may be difficult to achieve due to rapid ejection frequencies and the added complexity this would introduce into the system. Instead, a carefully-designed dispensing protocol backed by thorough inkjet characterization for the particular solution of interest is the recommended method to account for these effects.

Since individual drops weigh in the range of 10 nano grams to 1 micro gram, it is very difficult to determine their mass accurately, even in off-line mode. This problem is further complicated by complex geometry and machine design used for actual deposition of drops. Hence on-line measurement of drop size and feedback control during deposition is extremely challenging. As a result, a calibration scheme is employed where a large number of drops (5000 to 20000) is collected and weighed to determine the average mass of ejected drops. This scheme assumes that the drop mass remains the same no matter how many drops are ejected. Because of the discrepancy between calibration and actual deposition as described herein, the actual product does not receive the correct amount of the desired substance.

As described above, further complications with this discrepancy were discovered. It has been found that the weight of the first few drops changes as a function of the voltage amplitude used to create these drops. Hence the difference between the average mass calculated using the above calibration procedure and the average mass of first the 1 to 20 (approximately) drops changes as a function of voltage amplitude. This is graphically depicted in FIG. 14.

This happens because, within a sequence of drops, the weight of individual drops gradually increases and then plateaus out when operating in region A (see FIG. 17 which graphically illustrates one drop mass as a function or order of rejection within a burst for Region A of FIG. 14). The first of any burst of drops is significantly more sensitive to driving amplitude than later drops in a burst with its mass increasing much more rapidly than later drops as a function of driving amplitude. Thus, at amplitudes in Region C, the first drop in each burst is much larger than later drops. For small bursts of drops (e.g. the 5 drops per burst shown in FIG. 14), this larger first drop has a large impact and increases the average mass of the burst. However, for larger bursts of drops (e.g. the 800 drops per burst shown in FIG. 14) this effect is masked by the averaging effect of dispensing so many drops and so the response is linear. Because of this averaging effect, the average drop mass will be a function of the number of drops in a burst with the effect of the first drops being slowly diminished with larger and larger drop counts. Hence, a constant offset cannot be used to compensate for the discrepancy between calibration and actual drop deposition application since it will depend on how many drops are dispensed.

A number of methods may be utilized to correct for the first drop effect and achieve the correct amount of dispensed material during drop deposition applications. The present invention is directed to methods for depositing the exact same amount of a particular substance at various well defined locations on an object of interest. In the exemplary embodiment described herein, the well defined locations are the reservoirs and the object of interest is a stent. As described above, the jet deposits a number of drops at the location and then either the jet moves or the object moves so that either way the jet is over the next location.

As illustrated in FIG. 17, which illustrates the average drop mass for an entire sequence of drops as a function of time between adjacent bursts, depending on the region of operation (FIG. 14), the drop mass might first increase or decrease and then plateau out. Therefore, in accordance with a first exemplary method if the burst frequency and the jet/object movement can be controlled so that $Ts<Td$, wherein Ts is the time between two sequences of drops or the time needed to move the jet from location to location and Td is the time between the ejection of adjacent drops in a sequence of drops, however, since an initial burst frequency is used by the jets to generate drops, then Td equals 1/(burst frequency), then the first exemplary method outlined below may be utilized to obtain the same exact total drop mass at each location.

In the first step, a large number of drops is collected so that at the start of the filling process, the device is operating in the plateau region. This should only require the collection of a few hundred to a few thousand drops. From this the average drop weight may be calculated and this way the weight of the initial drops will not significantly change the average. In the second step, a calculation of how many drops will be needed to render the desired drop mass at each location is performed. In the third and final step, when the jet is turned on to start the actual drop deposition operation, the first few drops are collected in a waste collection container until the plateau region is reached and drops are deposited at every location while ensuring that $Ts<Td$. Since operation is now at the plateau region, consistent drop mass will be ensured.

As it may be difficult to meet the condition of $Ts<Td$ due to various factors including high dispensing frequency and limitations in servo speed and the like, a different methodology may be required. FIG. 18 graphically illustrates the average drop mass for an entire sequence of drops as a function of time between adjacent bursts. FIG. 18 illustrates that if enough time Tr, wherein Tr is the time needed for the first drop effect to reset, is allowed between consecutive sequences of drops, then the first drop effect can reset. Accordingly, if $Ts>Tr$, then every sequence of drops will have the same total weight. In this instance, the second exemplary methodology set forth below may be utilized and obtain or achieve the same total drop mass at every location.

In the first step, a large number of drops is collected by depositing sequences of drops in a collection container. This has to be done for many different cases where the number of drops in a sequence is changed from 1 to a large number to determine where the plateau for drop weight is achieved while making sure that for all drop sequences $Ts>Tr$ holds. Then the average drop weight for different drop numbers is determined. In the second step, a calculation is performed of how many drops will be needed to render the desired mass at each location. In the third and final step, drops are deposited at every location of the object by using the selected drop number above and making sure that $Ts>Tr$.

If neither of these conditions can be met, the difference between calibration by large numbers of drops and the dispensing process at small numbers of drops will remain. However, this may be accounted for in one of two ways. Determine the relationship shown in FIG. 14 for the specific process to understand the difference between the calibration and the dispensing process. The third exemplary method outlined below may be utilized to compensate for this difference mathematically by either applying more or less material than calculated by the calibration process depending on whether operation is in Region A or C. Alternately, ensure that calibration and dispensing process are identical for all parameters, including the number of drops in a sequence, so as not to introduce any bias. The first drop effect will still exist but it will be identical in both the calibration and dispensing process so the target material to be delivered will still be accurately achieved.

It is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any type of medical device may be coated in some fashion with a drug or drug combination which enhances treatment over use of the singular use of the device or pharmaceutical agent.

In addition to various medical devices, the coatings on these devices may be used to deliver any number of therapeutic and pharmaceutic agents. Some of the therapeutic agents for use with the present invention which may be transmitted primarily luminally, primarily murally, or both and may be delivered alone or in combination include, but are not limited to, antiproliferatives, antithrombins, immunosuppressants including sirolimus, antilipid agents, anti-inflammatory agents, antineoplastics, antiplatelets, angiogenic agents, anti-angiogenic agents, vitamins, antimitotics, metalloproteinase inhibitors, NO donors, estradiols, anti-sclerosing agents, and vasoactive agents, endothelial growth factors, estrogen, beta blockers, AZ blockers, hormones, statins, insulin growth factors, antioxidants, membrane stabilizing agents, calcium antagonists, retenoid, bivalirudin, phenoxodiol, etoposide, ticlopidine, dipyridamole, and trapidil alone or in combinations with any therapeutic agent mentioned herein. Therapeutic agents also include peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense, oligonucleotides, monoclonal antibodies, platelets, prions, viruses, bacteria, and eukaryotic cells such as endothelial cells, stem cells, ACE inhibitors, monocyte/macrophages or vascular smooth muscle cells to name but a few examples. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the therapeutic layer. Therapeutic agents may also be radioactive isotopes or agents activated by some other form of energy such as light or ultrasonic energy, or by other circulating molecules that can be systemically administered. Therapeutic agents may perform multiple functions including modulating angiogenesis, restenosis, cell proliferation, thrombosis, platelet aggregation, clotting, and vasodilation.

Anti-inflammatories include but are not limited to nonsteroidal anti-inflammatories (NSAID), such as aryl acetic acid derivatives, e.g., Diclofenac; aryl propionic acid derivatives, e.g., Naproxen; and salicylic acid derivatives, e.g., Diflunisal. Anti-inflammatories also include glucocoriticoids (steroids) such as dexamethasone, aspirin, prednisolone, and triamcinolone, pirfenidone, meclofenamic acid, tranilast, and nonsteroidal anti-inflammatories. Anti-inflammatories may be used in combination with antiproliferatives to mitigate the reaction of the tissue to the antiproliferative.

The agents may also include anti-lymphocytes; anti-macrophage substances; immunomodulatory agents; cyclooxygenase inhibitors; anti-oxidants; cholesterol-lowering drugs; statins and angiotens in converting enzyme (ACE); fibrinolytics; inhibitors of the intrinsic coagulation cascade; antihyperlipoproteinemics; and anti-platelet agents; anti-metabolites, such as 2-chlorodeoxy adenosine (2-CdA or cladribine); immuno-suppressants including sirolimus, everolimus, tacrolimus, etoposide, and mitoxantrone; anti-leukocytes such as 2-CdA, IL-1 inhibitors, anti-CD116/CD18 monoclonal antibodies, monoclonal antibodies to VCAM or ICAM, zinc protoporphyrin; anti-macrophage substances such as drugs that elevate NO; cell sensitizers to insulin including glitazones; high density lipoproteins (HDL) and derivatives; and synthetic facsimile of HDL, such as lipator, lovestatin, pranastatin, atorvastatin, simvastatin, and statin derivatives; vasodilators, such as adenosine, and dipyridamole; nitric oxide donors; prostaglandins and their derivatives; anti-TNF compounds; hypertension drugs including Beta blockers, ACE inhibitors, and calcium channel blockers; vasoactive substances including vasoactive intestinal polypeptides (VIP); insulin; cell sensitizers to insulin including glitazones, P par agonists, and metformin; protein kinases; antisense oligonucleotides including resten-NG; antiplatelet agents including tirofiban, eptifibatide, and abciximab; cardio protectants including, VIP, pituitary adenylate cyclase-activating peptide (PACAP), apoA-I milano, amlodipine, nicorandil, cilostaxone, and thienopyridine; cyclooxygenase inhibitors including COX-1 and COX-2 inhibitors; and petidose inhibitors which increase glycolitic metabolism including omnipatrilat. Other drugs which may be used to treat inflammation include lipid lowering agents, estrogen and progestin, endothelin receptor agonists and interleukin-6 antagonists, and Adiponectin.

Agents may also be delivered using a gene therapy-based approach in combination with an expandable medical device. Gene therapy refers to the delivery of exogenous genes to a cell or tissue, thereby causing target cells to express the exogenous gene product. Genes are typically delivered by either mechanical or vector-mediated methods.

Some of the agents described herein may be combined with additives which preserve their activity. For example additives including surfactants, antacids, antioxidants, and detergents may be used to minimize denaturation and aggregation of a protein drug. Anionic, cationic, or nonionic surfactants may be used. Examples of nonionic excipients include but are not limited to sugars including sorbitol, sucrose, trehalose; dextrans including dextran, carboxy methyl (CM) dextran, diethylamino ethyl (DEAE) dextran; sugar derivatives including D-glucosaminic acid, and D-glucose diethyl mercaptal; synthetic polyethers including polyethylene glycol (PEO) and polyvinyl pyrrolidone (PVP); carboxylic acids including D-lactic acid, glycolic acid, and propionic acid; surfactants with affinity for hydrophobic interfaces including n-dodecyl-.beta.-D-maltoside, n-octyl-.beta.-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; (PC) CM-PEG; cholic acid; sodium dodecyl sulfate (SDS); docusate (AOT); and taumocholic acid.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for depositing the same amount of a particular substance at a plurality of locations on an object, the method comprising:
   positioning the object in proximity to at least one jet of an ink-jet dispensing unit such that relative movement between the object and the at least one jet is achievable;
   delivering a first sequence of drops at a burst frequency;
   collecting a first number of drops of a first sequence of the particular substance from the at least one jet in a receptacle and determining an average drop mass;
   calculating how many drops are required to achieve a desired drop mass at each of the plurality of locations on the object;

delivering a second sequence of drops at the burst frequency;

collecting a second number of initial drops of a second sequence of the particular substance from the at least one jet in a receptacle, until steady state drop size is achieved; controlling the burst frequency and the relative movement between the object and the at least one jet such that a time interval needed to move between each of the plurality of locations is less than a time interval between consecutive drops of the second sequence, wherein each of the plurality of locations do not overlap with other locations of the plurality of locations; and depositing a number of subsequent drops of the second sequence required to achieve the desired drop mass at each of the plurality of locations on the object while maintaining the burst frequency when moving between each of the plurality of locations at the time interval that is less than the time interval between the consecutive drops of the second sequence.

* * * * *